(12) United States Patent
Turovskiy et al.

(10) Patent No.: US 11,213,678 B2
(45) Date of Patent: Jan. 4, 2022

(54) METHOD OF MANUFACTURING A MEDICAL DEVICE FOR NEUROMODULATION

(71) Applicant: Medtronic Ardian Luxembourg S.a.r.l., Luxembourg (LU)

(72) Inventors: Roman Turovskiy, San Francisco, CA (US); Maria Veronica Larios, East Palo Alto, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 190 days.

(21) Appl. No.: 16/290,565

(22) Filed: Mar. 1, 2019

(65) Prior Publication Data

US 2019/0192849 A1    Jun. 27, 2019

Related U.S. Application Data

(62) Division of application No. 14/021,838, filed on Sep. 9, 2013, now abandoned.

(51) Int. Cl.
*H01R 43/00* (2006.01)
*A61N 1/28* (2006.01)
(Continued)

(52) U.S. Cl.
CPC ............ *A61N 1/28* (2013.01); *A61B 18/1492* (2013.01); *A61B 2018/00404* (2013.01);
(Continued)

(58) Field of Classification Search
CPC ........... A61B 2018/00404; A61B 2018/00434; A61B 2018/00511; A61B 2018/00577;
(Continued)

(56) References Cited

U.S. PATENT DOCUMENTS 3,935,348 A    1/1976  Smith
4,154,246 A    5/1979  LeVeen
(Continued)

FOREIGN PATENT DOCUMENTS

CN    101583323    11/2009
CN    201469401    5/2010
(Continued)

OTHER PUBLICATIONS

Allen, E.V., Sympathectomy for essential hypertension, Circulation, 1952, 6:131-140.
(Continued)

*Primary Examiner* — Paul D Kim
(74) *Attorney, Agent, or Firm* — Shumaker & Sieffert, P.A.

(57) ABSTRACT

Catheter apparatuses, systems, and methods for achieving neuromodulation by intravascular access are disclosed herein. One aspect of the present technology, for example, is directed to a treatment device having a therapeutic assembly that includes an elongated tubular shaft having a pre-formed spiral shape when in a deployed state (e.g., a radially expanded, generally spiral/helical shape) and a thermocouple assembly helically wrapped about the shaft. In one embodiment, the thermocouple assembly comprises first and second wires composed of dissimilar metals with the first wire including a plurality of exposed and insulated regions along the distal portion of the treatment device. The exposed regions of the first wire define a plurality of energy delivery portions positioned to deliver electrical energy (e.g., RF energy, pulsed energy, etc.) to target tissue adjacent a wall of an artery (e.g., a renal artery) to heat or otherwise electrically modulate neural fibers that contribute to physiological function (e.g., renal function).

15 Claims, 11 Drawing Sheets

(51) Int. Cl.
*A61B 18/14* (2006.01)
*A61B 18/00* (2006.01)

(52) U.S. Cl.
CPC .............. *A61B 2018/00434* (2013.01); *A61B 2018/00511* (2013.01); *A61B 2018/00577* (2013.01); *A61B 2018/00821* (2013.01); *A61B 2018/144* (2013.01); *A61B 2018/1435* (2013.01); *Y10T 29/49002* (2015.01)

(58) Field of Classification Search
CPC .. A61B 2018/00821; A61B 2018/1435; A61B 2018/144; A61B 18/1492; A61N 1/28
See application file for complete search history.

(56) References Cited

U.S. PATENT DOCUMENTS

| | | |
|---|---|---|
| 4,169,464 A | 10/1979 | Obrez |
| 4,419,819 A | 12/1983 | Dickhudt et al. |
| 4,602,624 A | 7/1986 | Naples et al. |
| 4,649,936 A | 3/1987 | Ungar et al. |
| 4,660,571 A | 4/1987 | Hess et al. |
| 4,706,671 A | 11/1987 | Weinrib |
| 4,709,698 A | 12/1987 | Johnston et al. |
| 4,764,504 A | 8/1988 | Johnson et al. |
| 4,781,682 A | 11/1988 | Patel |
| 4,796,643 A | 1/1989 | Nakazawa et al. |
| 4,819,661 A | 4/1989 | Heil, Jr. et al. |
| 4,834,724 A | 5/1989 | Geiss et al. |
| 4,860,769 A | 8/1989 | Fogarty et al. |
| 4,890,623 A | 1/1990 | Cook et al. |
| 4,920,979 A | 5/1990 | Bullara |
| 4,921,484 A | 5/1990 | Hillstead |
| 4,957,118 A | 9/1990 | Erlebacher |
| 4,961,377 A | 10/1990 | Bando et al. |
| 4,966,597 A | 10/1990 | Cosman |
| 4,976,711 A | 12/1990 | Parins et al. |
| 4,995,868 A | 2/1991 | Brazier |
| 5,002,067 A | 3/1991 | Berthelsen et al. |
| 5,011,488 A | 4/1991 | Ginsburg |
| 5,016,808 A | 5/1991 | Heil, Jr. et al. |
| 5,052,998 A | 10/1991 | Zimmon |
| 5,054,501 A | 10/1991 | Chuttani et al. |
| 5,071,407 A | 12/1991 | Termin et al. |
| 5,071,424 A | 12/1991 | Reger |
| 5,133,365 A | 7/1992 | Heil, Jr. et al. |
| 5,156,151 A | 10/1992 | Imran |
| 5,156,610 A | 10/1992 | Reger |
| 5,158,564 A | 10/1992 | Schnepp-Pesch et al. |
| 5,163,928 A | 11/1992 | Hobbs et al. |
| 5,188,602 A | 2/1993 | Nichols |
| 5,188,619 A | 2/1993 | Myers |
| 5,209,723 A | 5/1993 | Twardowski et al. |
| 5,211,651 A | 5/1993 | Reger et al. |
| 5,228,442 A | 7/1993 | Imran |
| 5,239,999 A | 8/1993 | Imran |
| 5,249,585 A | 10/1993 | Turner et al. |
| 5,263,492 A | 11/1993 | Voyce |
| 5,263,493 A | 11/1993 | Avitall |
| 5,279,299 A | 1/1994 | Imran |
| 5,282,484 A | 2/1994 | Reger |
| 5,296,510 A | 3/1994 | Yamada et al. |
| 5,300,068 A | 4/1994 | Rosar et al. |
| 5,300,099 A | 4/1994 | Rudie |
| 5,308,323 A | 5/1994 | Sogawa et al. |
| 5,318,525 A | 6/1994 | West et al. |
| 5,324,284 A | 6/1994 | Imran |
| 5,327,905 A | 7/1994 | Avitall |
| 5,330,496 A | 7/1994 | Alferness |
| 5,345,031 A | 9/1994 | Schwartz et al. |
| 5,345,936 A | 9/1994 | Pomeranz et al. |
| 5,354,297 A | 10/1994 | Avitall |
| 5,358,514 A | 10/1994 | Schulman et al. |
| 5,365,926 A | 11/1994 | Desai |
| 5,368,591 A | 11/1994 | Lennox et al. |
| 5,383,856 A | 1/1995 | Bersin |
| 5,387,233 A | 2/1995 | Alferness |
| 5,397,304 A | 3/1995 | Truckai |
| 5,397,339 A | 3/1995 | Desai |
| 5,405,374 A | 4/1995 | Stein |
| 5,411,546 A | 5/1995 | Bowald et al. |
| 5,423,744 A | 6/1995 | Gencheff et al. |
| 5,427,118 A | 6/1995 | Nita et al. |
| 5,462,545 A | 10/1995 | Wang et al. |
| 5,476,495 A | 12/1995 | Kordis et al. |
| 5,476,498 A | 12/1995 | Ayers |
| 5,482,037 A | 1/1996 | Borghi |
| 5,484,400 A | 1/1996 | Edwards et al. |
| 5,487,385 A | 1/1996 | Avitall |
| 5,487,757 A | 1/1996 | Truckai et al. |
| 5,497,774 A | 3/1996 | Swartz et al. |
| 5,505,201 A | 4/1996 | Grill, Jr. et al. |
| 5,507,743 A | 4/1996 | Edwards et al. |
| 5,509,909 A | 4/1996 | Moy |
| 5,523,092 A | 6/1996 | Hanson et al. |
| 5,529,820 A | 6/1996 | Nomi et al. |
| 5,545,193 A | 8/1996 | Fleischman et al. |
| 5,545,200 A | 8/1996 | West et al. |
| 5,545,475 A | 8/1996 | Korleski |
| 5,549,661 A | 8/1996 | Kordis et al. |
| 5,564,440 A | 10/1996 | Swartz et al. |
| 5,571,147 A | 11/1996 | Sluijter et al. |
| 5,575,766 A | 11/1996 | Swartz et al. |
| 5,575,810 A | 11/1996 | Swanson et al. |
| 5,582,609 A | 12/1996 | Swanson et al. |
| 5,588,964 A | 12/1996 | Imran et al. |
| 5,591,132 A | 1/1997 | Carrie |
| 5,599,345 A | 2/1997 | Edwards et al. |
| 5,609,151 A | 3/1997 | Mulier et al. |
| 5,617,854 A | 4/1997 | Munsif |
| 5,626,576 A | 5/1997 | Janssen |
| 5,628,775 A | 5/1997 | Jackson |
| 5,636,634 A | 6/1997 | Kordis |
| 5,637,090 A | 6/1997 | McGee et al. |
| 5,642,736 A | 7/1997 | Avitall |
| 5,653,684 A | 8/1997 | Laptewicz et al. |
| 5,672,174 A | 9/1997 | Gough et al. |
| 5,676,662 A | 10/1997 | Fleischhacker et al. |
| 5,678,296 A | 10/1997 | Fleischhacker et al. |
| 5,680,860 A | 10/1997 | Imran |
| 5,681,280 A | 10/1997 | Rusk et al. |
| 5,687,723 A | 11/1997 | Avitall |
| 5,688,266 A | 11/1997 | Edwards et al. |
| 5,690,611 A | 11/1997 | Swartz et al. |
| 5,693,082 A | 12/1997 | Warner et al. |
| 5,697,928 A | 12/1997 | Walcott et al. |
| 5,700,282 A | 12/1997 | Zabara |
| 5,707,400 A | 1/1998 | Terry, Jr. et al. |
| 5,709,874 A | 1/1998 | Hanson et al. |
| 5,715,818 A | 2/1998 | Swartz et al. |
| 5,716,410 A | 2/1998 | Wang et al. |
| 5,722,401 A | 3/1998 | Pietroski et al. |
| 5,725,512 A | 3/1998 | Swartz et al. |
| 5,727,555 A | 3/1998 | Chait |
| 5,730,127 A | 3/1998 | Avitall |
| 5,730,741 A | 3/1998 | Horzewski et al. |
| 5,755,760 A | 5/1998 | Maguire et al. |
| 5,755,761 A | 5/1998 | Obino |
| 5,772,590 A | 6/1998 | Webster, Jr. |
| 5,800,494 A | 9/1998 | Campbell et al. |
| 5,807,395 A | 9/1998 | Mulier et al. |
| 5,814,028 A | 9/1998 | Swartz et al. |
| 5,823,955 A | 10/1998 | Kuck et al. |
| 5,827,242 A | 10/1998 | Follmer et al. |
| 5,827,268 A | 10/1998 | Laufer |
| 5,842,984 A | 12/1998 | Avitall |
| 5,846,355 A | 12/1998 | Spencer et al. |
| 5,860,920 A | 1/1999 | McGee et al. |
| 5,860,974 A | 1/1999 | Abele |
| 5,865,787 A | 2/1999 | Shapland |
| 5,865,815 A | 2/1999 | Tihon |
| 5,871,523 A | 2/1999 | Fleischman et al. |
| 5,871,531 A | 2/1999 | Struble |
| 5,873,865 A | 2/1999 | Horzewski et al. |

(56) References Cited

U.S. PATENT DOCUMENTS

| | | |
|---|---|---|
| 5,879,295 A | 3/1999 | Li et al. |
| 5,882,333 A | 3/1999 | Schaer et al. |
| 5,882,346 A | 3/1999 | Pomeranz et al. |
| 5,891,114 A | 4/1999 | Chien et al. |
| 5,893,885 A | 4/1999 | Webster, Jr. |
| 5,910,129 A | 6/1999 | Koblish et al. |
| 5,931,848 A | 8/1999 | Saadat |
| 5,938,694 A | 8/1999 | Jaraczewski et al. |
| 5,941,823 A | 8/1999 | Chait |
| 5,944,710 A | 8/1999 | Dev et al. |
| 5,951,471 A | 9/1999 | de la Rama et al. |
| 5,951,494 A | 9/1999 | Wang et al. |
| 5,951,539 A | 9/1999 | Nita et al. |
| 5,954,719 A | 9/1999 | Chen et al. |
| 5,957,961 A | 9/1999 | Maguire et al. |
| 5,968,085 A | 10/1999 | Morris et al. |
| 5,972,019 A | 10/1999 | Engelson et al. |
| 5,972,026 A | 10/1999 | Laufer et al. |
| 5,980,516 A | 11/1999 | Mulier et al. |
| 5,983,141 A | 11/1999 | Sluijter et al. |
| 5,993,462 A | 11/1999 | Pomeranz et al. |
| 5,997,526 A | 12/1999 | Giba et al. |
| 6,004,269 A | 12/1999 | Crowley et al. |
| 6,004,316 A | 12/1999 | Laufer |
| 6,004,348 A | 12/1999 | Banas et al. |
| 6,009,877 A | 1/2000 | Edwards |
| 6,012,457 A | 1/2000 | Lesh |
| 6,024,740 A | 2/2000 | Lesh et al. |
| 6,032,077 A | 2/2000 | Pomeranz |
| 6,036,687 A | 3/2000 | Laufer et al. |
| 6,042,578 A | 3/2000 | Dinh et al. |
| 6,048,329 A | 4/2000 | Thompson et al. |
| 6,064,902 A | 5/2000 | Haissaguerre et al. |
| 6,066,134 A | 5/2000 | Eggers et al. |
| 6,071,729 A | 6/2000 | Jeffries et al. |
| 6,074,339 A | 6/2000 | Gambale et al. |
| 6,074,361 A | 6/2000 | Jacobs |
| 6,074,378 A | 6/2000 | Mouri et al. |
| 6,076,012 A | 6/2000 | Swanson et al. |
| 6,078,830 A | 6/2000 | Levin et al. |
| 6,078,840 A | 6/2000 | Stokes |
| 6,078,841 A | 6/2000 | Kuzma |
| 6,090,104 A | 7/2000 | Webster, Jr. |
| 6,091,995 A | 7/2000 | Ingle et al. |
| 6,094,596 A | 7/2000 | Morgan |
| 6,096,036 A | 8/2000 | Bowe et al. |
| 6,099,524 A | 8/2000 | Lipson et al. |
| 6,106,522 A | 8/2000 | Fleischman et al. |
| 6,117,101 A | 9/2000 | Diederich et al. |
| 6,125,302 A | 9/2000 | Kuzma |
| 6,129,750 A | 10/2000 | Tockman et al. |
| 6,132,456 A | 10/2000 | Sommer et al. |
| 6,135,999 A | 10/2000 | Fanton et al. |
| 6,142,993 A | 11/2000 | Whayne et al. |
| 6,146,381 A | 11/2000 | Bowe et al. |
| 6,149,620 A | 11/2000 | Baker et al. |
| 6,152,912 A | 11/2000 | Jansen et al. |
| 6,156,046 A | 12/2000 | Passafaro et al. |
| 6,161,048 A | 12/2000 | Sluijter et al. |
| 6,161,049 A | 12/2000 | Rudie et al. |
| 6,162,184 A * | 12/2000 | Swanson ............ A61B 18/00 600/549 |
| 6,164,283 A | 12/2000 | Lesh |
| 6,190,356 B1 | 2/2001 | Bersin |
| 6,214,002 B1 | 4/2001 | Fleischman et al. |
| 6,219,577 B1 | 4/2001 | Brown, III et al. |
| 6,223,070 B1 | 4/2001 | Chait |
| 6,224,592 B1 | 5/2001 | Eggers et al. |
| 6,228,109 B1 | 5/2001 | Tu et al. |
| 6,246,912 B1 | 6/2001 | Sluijter et al. |
| 6,270,496 B1 | 8/2001 | Bowe et al. |
| 6,273,886 B1 | 8/2001 | Edwards et al. |
| 6,280,441 B1 | 8/2001 | Ryan |
| 6,283,951 B1 | 9/2001 | Flaherty et al. |
| 6,292,695 B1 | 9/2001 | Webster, Jr. et al. |
| 6,308,090 B1 | 10/2001 | Tu et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,325,797 B1 | 12/2001 | Stewart et al. |
| 6,364,904 B1 | 4/2002 | Smith |
| 6,385,472 B1 | 5/2002 | Hall et al. |
| 6,405,732 B1 | 6/2002 | Edwards et al. |
| 6,409,742 B1 | 6/2002 | Fulton, III et al. |
| 6,413,255 B1 | 7/2002 | Stern |
| 6,425,895 B1 | 7/2002 | Swanson et al. |
| 6,430,426 B2 | 8/2002 | Avitall |
| 6,436,056 B1 | 8/2002 | Wang et al. |
| 6,442,415 B1 | 8/2002 | Bis et al. |
| 6,451,045 B1 | 9/2002 | Walker et al. |
| 6,454,775 B1 | 9/2002 | Demarais et al. |
| 6,480,747 B2 | 11/2002 | Schmidt |
| 6,488,679 B1 | 12/2002 | Swanson et al. |
| 6,496,737 B2 | 12/2002 | Rudie et al. |
| 6,500,174 B1 | 12/2002 | Maguire et al. |
| 6,506,189 B1 | 1/2003 | Rittman et al. |
| 6,508,804 B2 | 1/2003 | Sarge et al. |
| 6,511,492 B1 | 1/2003 | Rosenbluth et al. |
| 6,514,226 B1 | 2/2003 | Levin et al. |
| 6,514,249 B1 | 2/2003 | Maguire et al. |
| 6,522,926 B1 | 2/2003 | Kieval et al. |
| 6,527,739 B1 | 3/2003 | Bigus et al. |
| 6,529,756 B1 | 3/2003 | Phan et al. |
| 6,530,935 B2 | 3/2003 | Wensel et al. |
| 6,540,734 B1 | 4/2003 | Chiu et al. |
| 6,542,781 B1 | 4/2003 | Koblish et al. |
| 6,546,272 B1 | 4/2003 | MacKinnon et al. |
| 6,546,280 B2 | 4/2003 | Osborne |
| 6,554,827 B2 | 4/2003 | Chandrasekaran et al. |
| 6,562,031 B2 | 5/2003 | Chandrasekaran et al. |
| 6,562,034 B2 | 5/2003 | Edwards et al. |
| 6,564,096 B2 | 5/2003 | Mest |
| 6,572,612 B2 | 6/2003 | Stewart et al. |
| 6,592,581 B2 | 7/2003 | Bowe |
| 6,602,242 B1 | 8/2003 | Fung et al. |
| 6,605,061 B2 | 8/2003 | VanTassel et al. |
| 6,607,520 B2 | 8/2003 | Keane |
| 6,610,046 B1 | 8/2003 | Usami et al. |
| 6,610,083 B2 | 8/2003 | Keller et al. |
| 6,613,046 B1 | 9/2003 | Jenkins et al. |
| 6,616,624 B1 | 9/2003 | Kieval |
| 6,622,731 B2 | 9/2003 | Daniel et al. |
| 6,623,515 B2 | 9/2003 | Mulier et al. |
| 6,628,976 B1 | 9/2003 | Fuimaono et al. |
| 6,635,054 B2 | 10/2003 | Fjield et al. |
| 6,640,120 B1 | 10/2003 | Swanson et al. |
| 6,652,517 B1 | 11/2003 | Hall et al. |
| 6,685,648 B2 | 2/2004 | Flaherty et al. |
| 6,692,490 B1 | 2/2004 | Edwards |
| 6,702,811 B2 | 3/2004 | Stewart et al. |
| 6,711,444 B2 | 3/2004 | Koblish |
| 6,736,835 B2 | 5/2004 | Pellegrino et al. |
| 6,745,080 B2 | 6/2004 | Koblish |
| 6,746,474 B2 | 6/2004 | Saadat |
| 6,752,805 B2 | 6/2004 | Maguire et al. |
| 6,758,830 B1 | 7/2004 | Schaer et al. |
| 6,773,433 B2 | 8/2004 | Stewart et al. |
| 6,780,183 B2 | 8/2004 | Jimenez, Jr. et al. |
| 6,802,840 B2 | 10/2004 | Chin et al. |
| 6,802,857 B1 | 10/2004 | Walsh et al. |
| 6,814,733 B2 | 11/2004 | Schwartz et al. |
| 6,817,999 B2 | 11/2004 | Berube et al. |
| 6,837,886 B2 | 1/2005 | Collins et al. |
| 6,845,267 B2 | 1/2005 | Harrison et al. |
| 6,847,848 B2 | 1/2005 | Sterzer et al. |
| 6,850,801 B2 | 2/2005 | Kieval et al. |
| 6,869,431 B2 | 3/2005 | Maguire et al. |
| 6,882,886 B1 | 4/2005 | Witte et al. |
| 6,885,888 B2 | 4/2005 | Rezai |
| 6,890,329 B2 | 5/2005 | Carroll et al. |
| 6,893,436 B2 | 5/2005 | Woodard et al. |
| 6,893,438 B2 | 5/2005 | Hall et al. |
| 6,899,711 B2 | 5/2005 | Stewart et al. |
| 6,905,510 B2 | 6/2005 | Saab |

(56) References Cited

U.S. PATENT DOCUMENTS

| | | |
|---|---|---|
| 6,909,920 B2 | 6/2005 | Lokhoff et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,941,953 B2 | 9/2005 | Feld et al. |
| 6,949,097 B2 | 9/2005 | Stewart et al. |
| 6,952,615 B2 | 10/2005 | Satake |
| 6,960,206 B2 | 11/2005 | Keane |
| 6,960,207 B2 | 11/2005 | Vanney et al. |
| 6,972,016 B2 | 12/2005 | Hill, III et al. |
| 7,013,169 B2 | 3/2006 | Bowe |
| 7,013,170 B2 | 3/2006 | Bowe |
| 7,058,456 B2 | 6/2006 | Pierce |
| 7,063,719 B2 | 6/2006 | Jansen et al. |
| 7,081,115 B2 | 7/2006 | Taimisto |
| 7,104,988 B2 | 9/2006 | Altman et al. |
| 7,110,828 B2 | 9/2006 | Kolberg et al. |
| 7,115,134 B2 | 10/2006 | Chambers |
| 7,149,574 B2 | 12/2006 | Yun et al. |
| 7,155,271 B2 | 12/2006 | Halperin et al. |
| 7,158,832 B2 | 1/2007 | Kieval et al. |
| 7,162,303 B2 | 1/2007 | Levin et al. |
| 7,184,811 B2 | 2/2007 | Phan et al. |
| 7,201,738 B1 | 4/2007 | Bengmark |
| 7,211,082 B2 | 5/2007 | Hall et al |
| 7,221,979 B2 | 5/2007 | Zhou et al. |
| 7,232,458 B2 | 6/2007 | Saadat |
| 7,254,451 B2 | 8/2007 | Seifert et al. |
| 7,264,619 B2 | 9/2007 | Venturelli |
| 7,282,213 B2 | 10/2007 | Schroeder et al. |
| 7,285,119 B2 | 10/2007 | Stewart et al. |
| 7,291,146 B2 | 11/2007 | Steinke et al. |
| 7,311,705 B2 | 12/2007 | Sra |
| 7,381,200 B2 | 6/2008 | Katoh et al. |
| 7,390,894 B2 | 6/2008 | Weinshilboum et al. |
| 7,404,824 B1 | 7/2008 | Webler et al. |
| 7,435,248 B2 | 10/2008 | Taimisto et al. |
| 7,517,349 B2 | 4/2009 | Truckai et al. |
| 7,526,343 B2 | 4/2009 | Peterson et al. |
| 7,542,808 B1 | 6/2009 | Peterson et al. |
| 7,597,704 B2 | 10/2009 | Frazier et al. |
| 7,617,005 B2 | 11/2009 | Demarais et al. |
| 7,620,451 B2 | 11/2009 | Demarais et al. |
| 7,637,903 B2 | 12/2009 | Lentz |
| 7,646,544 B2 | 1/2010 | Batchko et al. |
| 7,647,115 B2 | 1/2010 | Levin et al. |
| 7,647,124 B2 | 1/2010 | Williams et al. |
| 7,653,438 B2 | 1/2010 | Deem et al. |
| 7,670,335 B2 | 3/2010 | Keidar |
| 7,682,319 B2 | 3/2010 | Martin et al. |
| 7,717,853 B2 | 5/2010 | Nita |
| 7,717,948 B2 | 5/2010 | Demarais et al. |
| 7,727,178 B2 | 6/2010 | Wilson et al. |
| 7,729,782 B2 | 6/2010 | Williams et al. |
| 7,747,334 B2 | 6/2010 | Bly et al. |
| 7,771,421 B2 | 8/2010 | Stewart et al. |
| 7,778,703 B2 | 8/2010 | Gross et al. |
| 7,789,877 B2 | 9/2010 | Vanney |
| 7,806,871 B2 | 10/2010 | Li et al. |
| 7,850,685 B2 | 12/2010 | Kunis et al. |
| 7,863,897 B2 | 1/2011 | Slocum, Jr. et al. |
| 7,867,219 B2 | 1/2011 | Chambers |
| 7,881,807 B2 | 2/2011 | Schaer |
| 7,890,188 B2 | 2/2011 | Zhang et al. |
| 7,927,370 B2 | 4/2011 | Webler et al. |
| 7,942,928 B2 | 5/2011 | Webler et al. |
| 7,959,630 B2 | 6/2011 | Taimisto et al. |
| 8,019,435 B2 | 9/2011 | Hastings et al. |
| 8,062,284 B2 | 11/2011 | Booth |
| 8,100,859 B2 | 1/2012 | Patterson et al. |
| 8,123,739 B2 | 2/2012 | McQueen et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,428 B2 | 6/2012 | Truckai et al. |
| 8,257,351 B2 | 9/2012 | Stewart et al. |
| 8,308,722 B2 | 11/2012 | Ormsby et al. |
| 8,337,492 B2 | 12/2012 | Kunis et al. |
| 8,380,275 B2 | 2/2013 | Kim et al. |
| 8,398,629 B2 | 3/2013 | Thistle |
| 8,480,663 B2 | 7/2013 | Ingle et al. |
| 8,571,665 B2 | 10/2013 | Moffitt et al. |
| 8,868,209 B2 | 10/2014 | Clark et al. |
| 8,909,316 B2 | 12/2014 | Kok-Hwee et al. |
| 8,945,107 B2* | 2/2015 | Buckley .......... A61B 18/02 606/21 |
| 9,014,821 B2 | 4/2015 | Wang |
| 9,050,106 B2 | 6/2015 | Hill et al. |
| 9,055,956 B2 | 6/2015 | McRae et al. |
| 9,066,713 B2* | 6/2015 | Turovskiy .......... A61B 18/02 |
| 9,084,609 B2 | 7/2015 | Smith |
| 9,192,435 B2 | 11/2015 | Jenson et al. |
| 9,192,766 B2 | 11/2015 | Sobotka |
| 9,333,113 B2 | 5/2016 | Abunassar et al. |
| 10,188,445 B2* | 1/2019 | Buckley .......... A61B 18/02 |
| 10,736,690 B2* | 8/2020 | Kelly .......... A61B 18/1492 |
| 10,842,547 B2* | 11/2020 | Buckley .......... A61B 18/02 |
| 2001/0005785 A1 | 6/2001 | Sachse |
| 2001/0007070 A1 | 7/2001 | Stewart et al. |
| 2001/0020174 A1 | 9/2001 | Koblish |
| 2001/0031971 A1 | 10/2001 | Dretler et al. |
| 2002/0004631 A1 | 1/2002 | Jenkins et al. |
| 2002/0004644 A1 | 1/2002 | Koblish |
| 2002/0062124 A1 | 5/2002 | Keane |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill, III et al. |
| 2002/0169444 A1 | 11/2002 | Mest et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060857 A1 | 3/2003 | Perrson et al. |
| 2003/0060858 A1 | 3/2003 | Kieval et al. |
| 2003/0065317 A1 | 4/2003 | Rudie et al. |
| 2003/0074039 A1 | 4/2003 | Puskas |
| 2003/0088244 A1 | 5/2003 | Swanson et al. |
| 2003/0125790 A1 | 7/2003 | Fastovsky et al. |
| 2003/0153967 A1 | 8/2003 | Koblish |
| 2003/0158584 A1 | 8/2003 | Cates et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0204187 A1 | 10/2003 | Hintringer |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0024371 A1 | 2/2004 | Plicchi et al. |
| 2004/0030375 A1 | 2/2004 | Pierce |
| 2004/0049181 A1 | 3/2004 | Stewart et al. |
| 2004/0054363 A1 | 3/2004 | Vaska et al. |
| 2004/0082978 A1 | 4/2004 | Harrison et al. |
| 2004/0122421 A1 | 6/2004 | Wood |
| 2004/0167509 A1 | 8/2004 | Taimisto |
| 2004/0215186 A1 | 10/2004 | Cornelius et al. |
| 2005/0010095 A1 | 1/2005 | Stewart et al. |
| 2005/0015084 A1 | 1/2005 | Hill, III et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2005/0267465 A1 | 12/2005 | Hillier et al. |
| 2006/0074403 A1 | 4/2006 | Rafiee |
| 2006/0085054 A1 | 4/2006 | Zikorus et al. |
| 2006/0095029 A1 | 5/2006 | Young et al. |
| 2006/0135870 A1 | 6/2006 | Webler |
| 2006/0135953 A1 | 6/2006 | Kania et al. |
| 2006/0206150 A1 | 9/2006 | Demarais et al. |

(56) References Cited

U.S. PATENT DOCUMENTS

| | | |
|---|---|---|
| 2006/0212076 A1 | 9/2006 | Demarais et al. |
| 2006/0241366 A1 | 10/2006 | Falwell et al. |
| 2006/0247618 A1 | 11/2006 | Kaplan et al. |
| 2006/0247619 A1 | 11/2006 | Kaplan et al. |
| 2006/0271111 A1 | 11/2006 | Demarais et al. |
| 2007/0043409 A1 | 2/2007 | Brian, III et al. |
| 2007/0083194 A1 | 4/2007 | Kunis et al. |
| 2007/0106293 A1 | 5/2007 | Oral et al. |
| 2007/0129720 A1 | 6/2007 | Demarais et al. |
| 2007/0225781 A1 | 9/2007 | Saadat et al. |
| 2007/0265687 A1 | 11/2007 | Deem et al. |
| 2008/0021408 A1 | 1/2008 | Jacobsen et al. |
| 2008/0045921 A1 | 2/2008 | Anderson et al. |
| 2008/0064957 A1 | 3/2008 | Spence |
| 2008/0097398 A1 | 4/2008 | Mitelberg et al. |
| 2008/0108975 A1 | 5/2008 | Appling et al. |
| 2008/0109011 A1 | 5/2008 | Thenuwara et al. |
| 2008/0172104 A1 | 7/2008 | Kieval et al. |
| 2008/0255539 A1 | 10/2008 | Booth |
| 2008/0288039 A1 | 11/2008 | Reddy |
| 2008/0300587 A1 | 12/2008 | Anderson |
| 2008/0319513 A1 | 12/2008 | Pu et al. |
| 2009/0018534 A1 | 1/2009 | Taimisto et al. |
| 2009/0036948 A1 | 2/2009 | Levin et al. |
| 2009/0157066 A1* | 6/2009 | Satake .................. A61B 18/04 606/27 |
| 2009/0287202 A1 | 11/2009 | Ingle et al. |
| 2009/0306650 A1 | 12/2009 | Govari et al. |
| 2009/0312606 A1 | 12/2009 | Dayton et al. |
| 2010/0030112 A1 | 2/2010 | Anderson et al. |
| 2010/0137860 A1 | 6/2010 | Demarais et al. |
| 2010/0137952 A1 | 6/2010 | Demarais et al. |
| 2010/0168777 A1 | 7/2010 | Stangenes et al. |
| 2010/0174282 A1 | 7/2010 | Demarais et al. |
| 2010/0179512 A1 | 7/2010 | Chong et al. |
| 2010/0191112 A1 | 7/2010 | Demarais et al. |
| 2010/0204692 A1 | 8/2010 | Stewart et al. |
| 2010/0222851 A1 | 9/2010 | Deem et al. |
| 2010/0222854 A1 | 9/2010 | Demarais et al. |
| 2010/0261990 A1 | 10/2010 | Gillis et al. |
| 2011/0021976 A1 | 1/2011 | Li et al. |
| 2011/0144639 A1 | 6/2011 | Govari |
| 2011/0160719 A1 | 6/2011 | Govari et al. |
| 2011/0264086 A1 | 10/2011 | Ingle |
| 2011/0306851 A1 | 12/2011 | Wang |
| 2011/0319908 A1 | 12/2011 | Thenuwara et al. |
| 2012/0010607 A1 | 1/2012 | Malecki et al. |
| 2012/0029509 A1 | 2/2012 | Smith |
| 2012/0029510 A1 | 2/2012 | Haverkost |
| 2012/0029513 A1 | 2/2012 | Smith et al. |
| 2012/0035615 A1 | 2/2012 | Koester et al. |
| 2012/0078076 A1 | 3/2012 | Stewart et al. |
| 2012/0089123 A1* | 4/2012 | Organ ................ A61B 18/1492 604/523 |
| 2012/0101553 A1 | 4/2012 | Reddy |
| 2012/0116382 A1 | 5/2012 | Ku et al. |
| 2012/0116383 A1 | 5/2012 | Mauch et al. |
| 2012/0116438 A1 | 5/2012 | Salahieh et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130368 A1 | 5/2012 | Jenson |
| 2012/0143293 A1 | 6/2012 | Mauch et al. |
| 2012/0172837 A1 | 7/2012 | Demarais et al. |
| 2012/0191083 A1 | 7/2012 | Moll et al. |
| 2012/0197246 A1 | 8/2012 | Mauch |
| 2012/0277842 A1 | 11/2012 | Kunis |
| 2012/0290053 A1 | 11/2012 | Zhang et al. |
| 2012/0310065 A1 | 12/2012 | Falwell et al. |
| 2012/0310239 A1 | 12/2012 | Stewart et al. |
| 2012/0323233 A1 | 12/2012 | Maguire et al. |
| 2013/0053876 A1 | 2/2013 | Ogle |
| 2013/0066316 A1 | 3/2013 | Steinke et al. |
| 2013/0085360 A1 | 4/2013 | Grunewald |
| 2013/0090637 A1 | 4/2013 | Sliwa |
| 2013/0144283 A1 | 6/2013 | Barman |
| 2013/0165920 A1 | 6/2013 | Weber et al. |
| 2013/0165921 A1 | 6/2013 | Sutermeister et al. |
| 2013/0172872 A1 | 7/2013 | Subramaniam et al. |
| 2013/0172879 A1 | 7/2013 | Sutermeister et al. |
| 2013/0184703 A1 | 7/2013 | Shireman et al. |
| 2013/0184773 A1 | 7/2013 | Libbus et al. |
| 2013/0253628 A1 | 9/2013 | Smith et al. |
| 2013/0274614 A1 | 10/2013 | Shimada et al. |
| 2013/0274730 A1 | 10/2013 | Anderson et al. |
| 2013/0274731 A1 | 10/2013 | Anderson et al. |
| 2013/0274737 A1 | 10/2013 | Wang et al. |
| 2013/0282000 A1 | 10/2013 | Parsonage |
| 2013/0282084 A1 | 10/2013 | Mathur et al. |
| 2013/0289686 A1 | 10/2013 | Masson et al. |
| 2013/0304047 A1 | 11/2013 | Grunewald et al. |
| 2013/0304052 A1 | 11/2013 | Rizq et al. |
| 2013/0304062 A1 | 11/2013 | Chan et al. |
| 2014/0058376 A1 | 2/2014 | Horn et al. |
| 2014/0213873 A1 | 7/2014 | Wang |
| 2014/0214018 A1 | 7/2014 | Behar et al. |
| 2014/0221805 A1 | 8/2014 | Wang |
| 2014/0243821 A1 | 8/2014 | Salahieh et al. |
| 2014/0249524 A1 | 9/2014 | Kocur |
| 2014/0257280 A1 | 9/2014 | Hanson et al. |
| 2014/0257281 A1 | 9/2014 | Squire et al. |
| 2014/0276747 A1 | 9/2014 | Abunassar et al. |
| 2014/0276748 A1 | 9/2014 | Ku et al. |
| 2014/0276752 A1 | 9/2014 | Wang et al. |
| 2014/0276787 A1 | 9/2014 | Wang et al. |
| 2014/0276789 A1 | 9/2014 | Dandler et al. |
| 2014/0303617 A1 | 10/2014 | Shimada |
| 2014/0350553 A1 | 11/2014 | Okuyama |
| 2015/0025525 A1 | 1/2015 | Willard et al. |
| 2015/0057655 A1 | 2/2015 | Osypka |
| 2015/0066013 A1 | 3/2015 | Salahieh et al. |
| 2015/0105659 A1 | 4/2015 | Salahieh et al. |
| 2015/0112329 A1 | 4/2015 | Ng |
| 2015/0126992 A1 | 5/2015 | Mogul |
| 2015/0223866 A1 | 8/2015 | Buelna et al. |
| 2015/0223877 A1 | 8/2015 | Behar et al. |
| 2015/0289770 A1 | 10/2015 | Wang |
| 2016/0175040 A1 | 6/2016 | Magana et al. |
| 2016/0175044 A1 | 6/2016 | Abunassar et al. |
| 2016/0175582 A1 | 6/2016 | Serna et al. |
| 2016/0374568 A1 | 12/2016 | Wang |
| 2017/0042610 A1 | 2/2017 | Smith et al. |

FOREIGN PATENT DOCUMENTS

| | | |
|---|---|---|
| CN | 102198015 | 9/2011 |
| CN | 102274075 | 12/2011 |
| CN | 102488552 | 6/2012 |
| CN | 202386778 | 8/2012 |
| CN | 202426649 | 9/2012 |
| CN | 202537649 | 11/2012 |
| CN | 202538132 | 11/2012 |
| CN | 102885648 | 1/2013 |
| CN | 102885649 | 1/2013 |
| CN | 102908188 | 2/2013 |
| CN | 102908189 | 2/2013 |
| CN | 202761434 | 3/2013 |
| CN | 103027745 | 4/2013 |
| CN | 103027746 | 4/2013 |
| CN | 202843784 | 4/2013 |
| CN | 102772249 | 1/2015 |
| CN | 105167840 | 12/2015 |
| CN | 105326562 | 2/2016 |
| CN | 205433878 | 8/2016 |
| CN | 205433879 | 8/2016 |
| DE | 29909082 | 7/1999 |
| DE | 10252325 | 5/2004 |
| DE | 10257146 | 6/2004 |
| EP | 0132344 | 1/1985 |
| EP | 510624 | 10/1992 |
| EP | 732080 | 9/1996 |
| EP | 779079 | 6/1997 |
| EP | 821602 | 2/1998 |
| EP | 865256 | 9/1998 |

(56) References Cited

FOREIGN PATENT DOCUMENTS

| | | |
|---|---|---|
| EP | 868160 | 10/1998 |
| EP | 868923 | 10/1998 |
| EP | 0868923 | 10/1998 |
| EP | 728495 | 4/1999 |
| EP | 0916360 | 5/1999 |
| EP | 916360 | 5/1999 |
| EP | 1042990 | 10/2000 |
| EP | 1233716 | 8/2002 |
| EP | 1297795 | 4/2003 |
| EP | 963191 | 8/2003 |
| EP | 1332724 | 8/2003 |
| EP | 757575 | 9/2003 |
| EP | 873760 | 1/2004 |
| EP | 1383567 | 1/2004 |
| EP | 778043 | 11/2005 |
| EP | 1733689 | 12/2006 |
| EP | 1802370 | 7/2007 |
| EP | 1009303 | 6/2009 |
| EP | 2208474 | 7/2010 |
| EP | 2263588 | 12/2010 |
| EP | 2329859 | 6/2011 |
| EP | 2519173 | 11/2012 |
| EP | 2558016 | 2/2013 |
| EP | 2570154 | 3/2013 |
| EP | 2598069 | 6/2013 |
| EP | 2664295 | 11/2013 |
| EP | 2694158 | 2/2014 |
| EP | 2759275 | 7/2014 |
| EP | 2760532 | 8/2014 |
| EP | 2804554 | 11/2014 |
| EP | 2839802 | 2/2015 |
| EP | 2890321 | 7/2015 |
| EP | 2907464 | 8/2015 |
| EP | 3003191 | 4/2016 |
| EP | 3049007 | 8/2016 |
| EP | 2645955 | 10/2016 |
| EP | 2836151 | 10/2016 |
| EP | 3102132 | 12/2016 |
| EP | 2709517 | 1/2017 |
| EP | 3123973 | 2/2017 |
| EP | 3148467 | 4/2017 |
| JP | 355134141 | 10/1980 |
| JP | 2015119831 | 7/2015 |
| JP | 2016086999 | 5/2016 |
| WO | WO1991015254 | 10/1991 |
| WO | WO1992020291 | 11/1992 |
| WO | WO1994007446 | 4/1994 |
| WO | WO1994021168 | 9/1994 |
| WO | WO1995013111 | 5/1995 |
| WO | WO1995020416 | 8/1995 |
| WO | WO1995025472 | 9/1995 |
| WO | WO1995031142 | 11/1995 |
| WO | WO96000036 | 1/1996 |
| WO | WO1996000036 | 1/1996 |
| WO | WO1996032980 | 10/1996 |
| WO | WO1996038196 | 12/1996 |
| WO | WO1997017892 | 5/1997 |
| WO | WO1997036548 | 10/1997 |
| WO | WO1998002201 | 1/1998 |
| WO | WO1998018393 | 5/1998 |
| WO | WO1998033469 | 8/1998 |
| WO | WO1998042403 | 10/1998 |
| WO | WO1998043530 | 10/1998 |
| WO | WO1999000060 | 1/1999 |
| WO | WO1999023958 | 5/1999 |
| WO | WO1999052421 | 10/1999 |
| WO | WO1999056801 | 11/1999 |
| WO | WO1999062413 | 12/1999 |
| WO | WO00001313 | 1/2000 |
| WO | WO2000001313 | 1/2000 |
| WO | WO00056237 | 9/2000 |
| WO | WO00067832 | 11/2000 |
| WO | WO2001022897 | 4/2001 |
| WO | WO01037746 | 5/2001 |
| WO | WO2001037723 | 5/2001 |
| WO | WO2001037746 | 5/2001 |
| WO | WO2001070114 | 9/2001 |
| WO | WO2001074255 | 10/2001 |
| WO | WO01080758 | 11/2001 |
| WO | WO2002045608 | 6/2002 |
| WO | WO2002083017 | 10/2002 |
| WO | WO2002087453 | 11/2002 |
| WO | WO2002089687 | 11/2002 |
| WO | WO2002089908 | 11/2002 |
| WO | WO2003022167 | 3/2003 |
| WO | WO20030777781 | 9/2003 |
| WO | WO2003082080 | 10/2003 |
| WO | WO2004100813 | 11/2004 |
| WO | WO2005030072 | 4/2005 |
| WO | WO2005041748 | 5/2005 |
| WO | WO2005051216 | 6/2005 |
| WO | WO2005070491 | 8/2005 |
| WO | WO2005110528 | 11/2005 |
| WO | WO2006020920 | 2/2006 |
| WO | WO2006041881 | 4/2006 |
| WO | WO2006065949 | 6/2006 |
| WO | WO2006092000 | 9/2006 |
| WO | WO2006105121 | 10/2006 |
| WO | WO2007001981 | 1/2007 |
| WO | WO2007008954 | 1/2007 |
| WO | WO2007078997 | 7/2007 |
| WO | WO2007128064 | 11/2007 |
| WO | WO2008049084 | 4/2008 |
| WO | WO2008101244 | 8/2008 |
| WO | WO2009121017 | 1/2009 |
| WO | WO2009082635 | 7/2009 |
| WO | WO2010048676 | 5/2010 |
| WO | WO2010091701 | 8/2010 |
| WO | WO2010120835 | 10/2010 |
| WO | WO2011015218 | 2/2011 |
| WO | WO2011019838 | 2/2011 |
| WO | WO2011055143 | 5/2011 |
| WO | WO2011060200 | 5/2011 |
| WO | WO2011082279 | 7/2011 |
| WO | WO2011130534 | 10/2011 |
| WO | WO2012075156 | 6/2012 |
| WO | WO2012130337 | 10/2012 |
| WO | WO2012131107 | 10/2012 |
| WO | WO2012154219 | 11/2012 |
| WO | WO2012154796 | 11/2012 |
| WO | WO2013016203 | 1/2013 |
| WO | WO2013028993 | 2/2013 |
| WO | WO2013030807 | 3/2013 |
| WO | WO2013040201 | 3/2013 |
| WO | WO2013049604 | 4/2013 |
| WO | WO2013101452 | 7/2013 |
| WO | WO2013106054 | 7/2013 |
| WO | WO2013109318 | 7/2013 |
| WO | 2013134479 A1 | 9/2013 |
| WO | 2013134492 A1 | 9/2013 |
| WO | 2013134541 A2 | 9/2013 |
| WO | 2013134548 A2 | 9/2013 |
| WO | WO2013154776 | 10/2013 |
| WO | WO2013158676 | 10/2013 |
| WO | WO2013158678 | 10/2013 |
| WO | WO2013165920 | 11/2013 |
| WO | WO2014036160 | 3/2014 |
| WO | WO2014036163 | 3/2014 |
| WO | WO2014056460 | 4/2014 |
| WO | WO0214163987 | 10/2014 |
| WO | WO2014163990 | 10/2014 |
| WO | WO2014176785 | 11/2014 |
| WO | WO2015161790 | 10/2015 |
| WO | WO2016094938 | 6/2016 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation of Proximal Water and Sodium Reabsorption," Journal of Clinical Investigation, vol. 57, Apr. 1976, pp. 1104-1107.

(56) References Cited

OTHER PUBLICATIONS

Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertenstion After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part2, 2002 American Heart Association, Inc., pp. 621-624.
Janssen, Ben J.A. et al., "Effects of Complete Renal Denervation and Selective Afferent Renal Denervation of the Hypertension Induced by Intrarenal Norepinephrine Infusion in Conscious Rats", Journal of Hypertension, Jul. 1989: 447-445.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373: 1275-81.
Krum, et al., "Renal Sympathetic-Nerve Amblation for Uncontrolled Hypertension." New England Journal of Med, Aug. 2009, 361; 9, 3 pages.
Luippold, Gerd et al., "Chronic Renal Denervation Prevents Glomerular Hyperfilteration in Diabetic Rats", Nephrol Dial Transplant, vol. 19, No. 2, 2004, pp. 342-347.
Mahfoud et al. "Treatment strategies for resistant arterial hyperension" Dtsch Arztebl Int. 2011;108:725-731.
Osborn, et al., "Effect of Renal Nerve Stimulation on Renal Blood Flow Autoregulation and Antinatriuresis During Deductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Simplicity Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953, 152:1501-1504.
Symplicity HTN-1 Investigators; Krum H, Barman H, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al,, "Laparoscopic Renal Denervation for Intractable ADPKD-Related , Pain", Nephrol Dial Transplant (2001) 16: 1 pages.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: Apr. 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. 2465470, Granted Oct. 28, 2015, Date of Opposition Jul. 27, 2016, 34 pp.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper, et al., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, Jun. 2002, 4 pages.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.

(56) References Cited

OTHER PUBLICATIONS

Wittkampf et al., "Control of radiofrequency lesion size by power regulation," Journal of the American Heart Associate, 1989, 80: pp. 962-968.
Zheng et al., "Comparison of the temperature profile and pathological effect at an unipolar, bipolar and phased radiofrequency current configurations," Journal of the Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 Top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year," Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberia—Renal Sympathetic Denervation System: Turning innovation into quality care." [Brochure], Terumo Europe N.V., 2013, Europe, 3 pages.
"Neurotech Neurotech Reports Announces Winners of Gold Electrode Awards." Neurotech business 2009, 1 page, <http://www.neurotechreports.com/pages/goldelectrodes09.html>.
"Quick, Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy fol Resistant Hypertension." Journal of the American College of Cardiology, vol. 62, No. 3, 2013, 11 pages.
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension," Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery embolization with diluted hot contrast medium: An experimental study." J Vasc Interv Radiol, 12: 862-868 (2001) .
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response," *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honor for renal denervation system." The official bldg of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.

(56) References Cited

OTHER PUBLICATIONS

Kompanowska, E., et al., "Early Effects of renal denervation in the anaesthetised rat: Natriuresis and increased cortical blood flow." J Physiol, 531. 2:527-534 (2001).
Lee, S. J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D. L., et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofriquency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt is the Beginning of Wisdom)", Circulation Research, 2014; 115: 211-214.
Papademetriou, Vasilios et al., "Renal Nerve Ablation for Resistant Hypertenstion: How Did We Get Here, Present Status, and Future Directions." Circulation. 2014; 129: 1440-1450.
Papademetriou, Vasillos et al., "Catheter-Based Renal Denervation for Resistant Hypertension: 12-Month Results of the EnligHTN I First-in-Human Study Using Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
European European Search Report dated Jan. 30, 2013; European Application No. 12180426.4; Applicant: Medtronic Ardian Luxembourg S.a.r.l.; 6 pages.
European Search Report dated Feb. 28, 2013; European Application No. 12180427.2; Applcant: Medtronic Ardian Luxembourg S.a.r.l.; 4 pages.
European Search Report dated Jan. 30, 2013; Application No. 12180428.0; Applicant: Medtronic Ardian Luxembourg S.a.r.l.; 6 pages.
European Search Report dated Jan. 30, 2013; Application No. 12180430.6; Applicant: Medtronic Ardian Luxembourg S.A.r.l.: 6 pages.
European Search Report dated Jan. 30, 2013; Application No. 12180431.4; Applicant: Medtronic Ardian Luxembourg S.A.r.l.; 6 pages.
European Search Report dated Feb. 22, 2013: Application No. 12180432.2; Applicant: Medtronic Ardian Luxembourg S.a.r.l.; 6 pages.
Hanker et al., "Biomedical Materials and Devices," Materials Research Society Symposium Proceedings, vol. 110, Dec. 4, 1987, Boston Massachusetts, USA, 8 pages.
Claudine Jaboro, "An in vivo study of the biocompatibility of classic and novel device materials on the central nervous system", (Jan. 1, 2007), ETD Collection for Wayne State University, Paper AAI3310737, 2 pages. <http://digitalcommons.wayne.edu/dissertations/AAI3310737>.

(56) References Cited

OTHER PUBLICATIONS

Lahiri D. et al. Boron nitride nanotube reinforced polylactide-polycaprolactone copolymer composite: Mechanical properties and cytocompatibility with osteoblasts and macrophages in vitro. Acta Biomater (2010). doi: 10.1016/j.actbio.2010.02.44.
Search Report and Written Opinion dated Jan. 23, 2012 for PCT Application No. PCT/US2011/057761.
Search Report and Written Opinion dated Jan. 20, 2012 for PCT Application No. PCT/US2011/057756.
Search Report and Written Opinion dated Feb. 16, 2012 for PCT Application No. PCT/US2011/057754.
Search Report and Written Opinion dated Dec. 5, 2014 for PCT Application No. PCT/US2014/054654.
International Search Report, PCT/US02/07661, dated Aug. 13, 2002, 5 Pages.
International Search Report, PCT/US03/031339, dated Feb. 18, 2004, 3 Pages.
International Search Report, PCT/US01/044977, dated Jun. 7, 2002, 6 Pages.

\* cited by examiner

METHOD OF MANUFACTURING A MEDICAL DEVICE FOR NEUROMODULATION

CROSS-REFERENCE TO RELATED APPLICATIONS

This application is a Divisional of U.S. patent application Ser. No. 14/021,838, filed Sep. 9, 2013, now abandoned, the disclosure of which is incorporated herein by reference in its entirety.

TECHNICAL FIELD

The present technology relates generally to neuromodulation and associated systems and methods. In particular, several embodiments are directed to catheters having energy delivering thermocouple assemblies for intravascular neuromodulation and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via radiofrequency ablation) have been shown to reduce blood pressure in patients with treatment-resistant hypertension.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers may be used to identify identical or at least generally similar or analogous components or features.

DETAILED DESCRIPTION

Figure 1A:
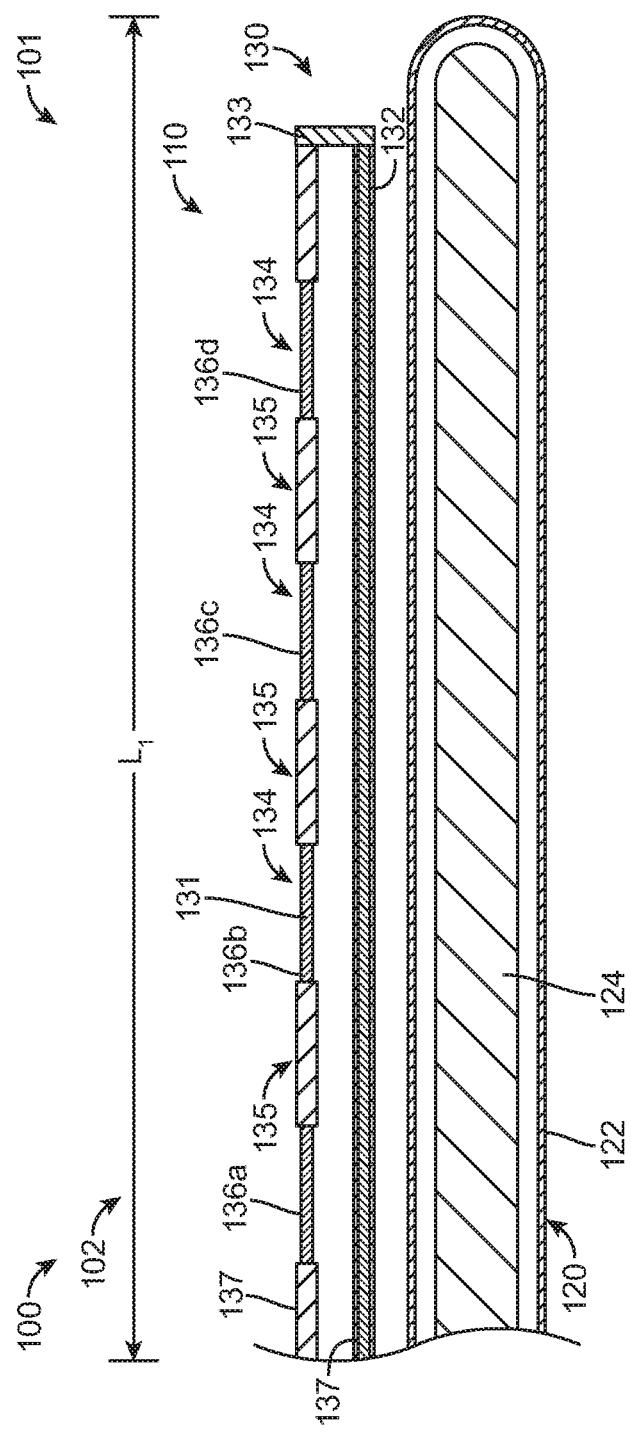
FIG. 1A is an enlarged cross-sectional side view illustrating a therapeutic assembly of a neuromodulation catheter apparatus following a step in a process for assembling the therapeutic assembly from an unassembled state outside a patient in accordance with an embodiment of the present technology.

The present technology is directed to apparatuses, systems, and methods for achieving thermally-induced neuromodulation (i.e., rendering neural fibers that innervate, for example, the kidney or another physiological organ or structure inert or inactive or otherwise completely or partially reduced in function) by percutaneous transluminal intravascular access. In particular, embodiments of the present technology relate to catheters and catheter assemblies having energy delivering thermocouple assemblies and being movable between a delivery or low-profile state (e.g., a generally straight shape) and a deployed state (e.g., a radially expanded shape, generally spiral/helical shape, an expanded lasso shape, J-shape, etc.). The thermocouple assembly may include a plurality of non-insulated energy-delivery portions of a first thermocouple wire (e.g., a silver-coated nickel wire, a silver wire, a nickel wire, a copper wire with biocompatible coating thereon, etc.) that can be coupled to or otherwise extend along or about a longitudinal dimension of a catheter shaft, and may include a second insulated thermocouple wire (e.g., a constantan wire) for thermocouple functionality. The thermocouple assembly is in electrical communication with an energy source or energy generator such that energy is delivered from the non-insulated energy delivery portions of the first thermocouple wire to portions of an artery after being advanced thereto via a catheter along a percutaneous transluminal path (e.g., a femoral artery puncture, an iliac artery and the aorta, a radial artery, or another suitable intravascular path). Any suitable energy modality may be used (e.g., electrical energy such as radiofrequency (RF) energy, pulsed energy, etc.). The catheter or catheter assembly carrying the thermocouple assembly may be sized and shaped so that the non-insulated energy delivery portions contact an interior wall of an artery (e.g., a renal artery, an ovarian artery, testicular artery, external iliac artery, internal iliac artery, internal pudendal artery, uterine artery, celiac artery, superior mesenteric artery, hepatic artery, splenic artery, gastric artery, pancreatic artery, and/or associated arterial branches, etc.) when the catheter is in the deployed state within the artery. The pre-formed expanded shape (e.g., spiral/helical, lasso, J-shape, etc.) of the deployed portion of the catheter carrying the thermocouple assembly allows blood to flow through the helix, which is expected to help avoid occlusion of the artery during activation of the non-insulated energy delivery portions of the thermocouple wire.

Energy-delivery catheter systems for inducing neuromodulation that include separate electrodes or arrays of electrodes can be expensive to manufacture. These designs may require separate wiring of each electrode to a conventional thermocouple wire, as well as complex algorithms and energy generator designs to operate. In contrast, the thermocouple assembly presented herein includes a single energy delivering wire (e.g., the first wire) that can have direct electrical communication with an energy generator, and each non-insulated energy delivery portion of the single wire is in electrical communication with each of the other non-insulated energy delivery portions along the wire. This is expected to reduce manufacturing time and material costs associated with separate electrodes and wiring, as well as reduce the complexity of the control algorithm typically necessary to operate more than one independent electrode or energy delivery element.

Specific details of several embodiments of the technology are described below with reference to FIGS. 1A-5. Although many of the embodiments are described below with respect to devices, systems, and methods for intravascular modulation of sympathetic nerves using thermocouple assemblies, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1A-5.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal" and "proximally" are a position near or in a direction toward the clinician or clinician's control device.

Selected Examples of Catheters and Related Devices

Figure 1B:
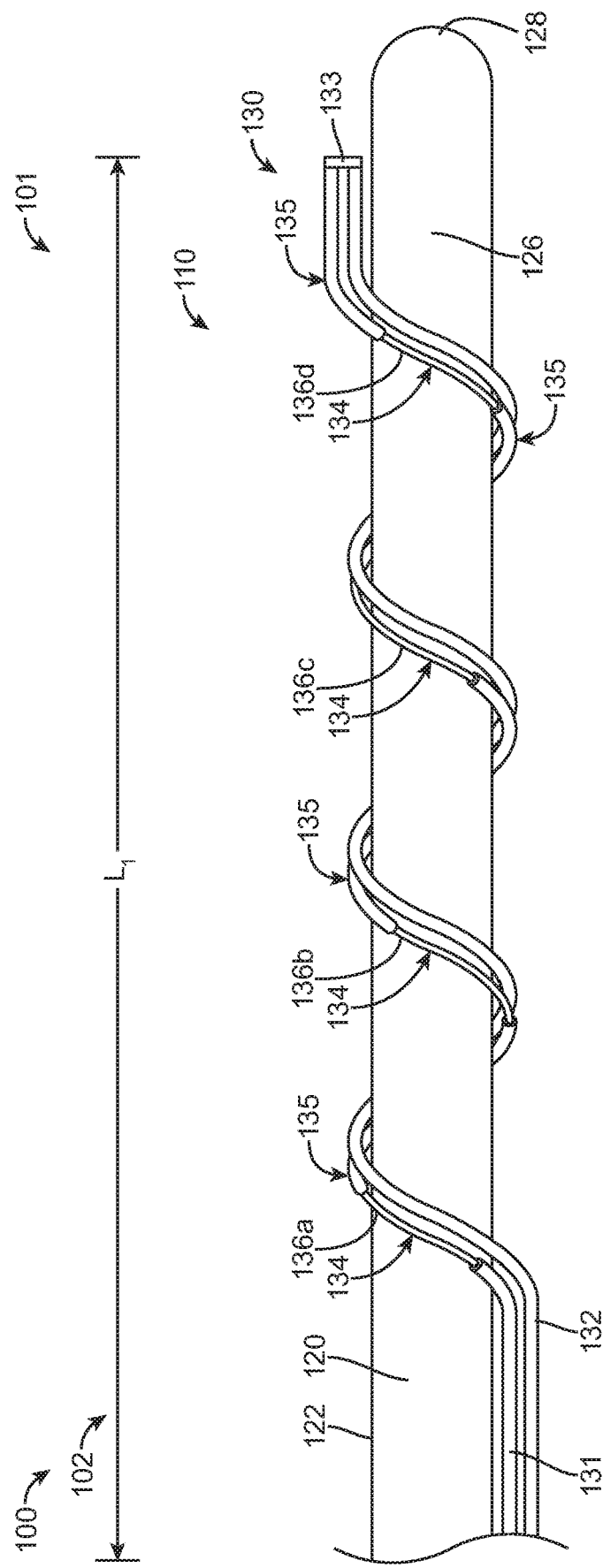
FIG. 1B is a side view of the therapeutic assembly of the catheter apparatus shown in FIG. 1A, following another step in the assembly process of the therapeutic assembly, with the therapeutic assembly shown in a delivery state (e.g., low-profile or collapsed configuration) in accordance with an embodiment of the present technology.
Figure 1C:
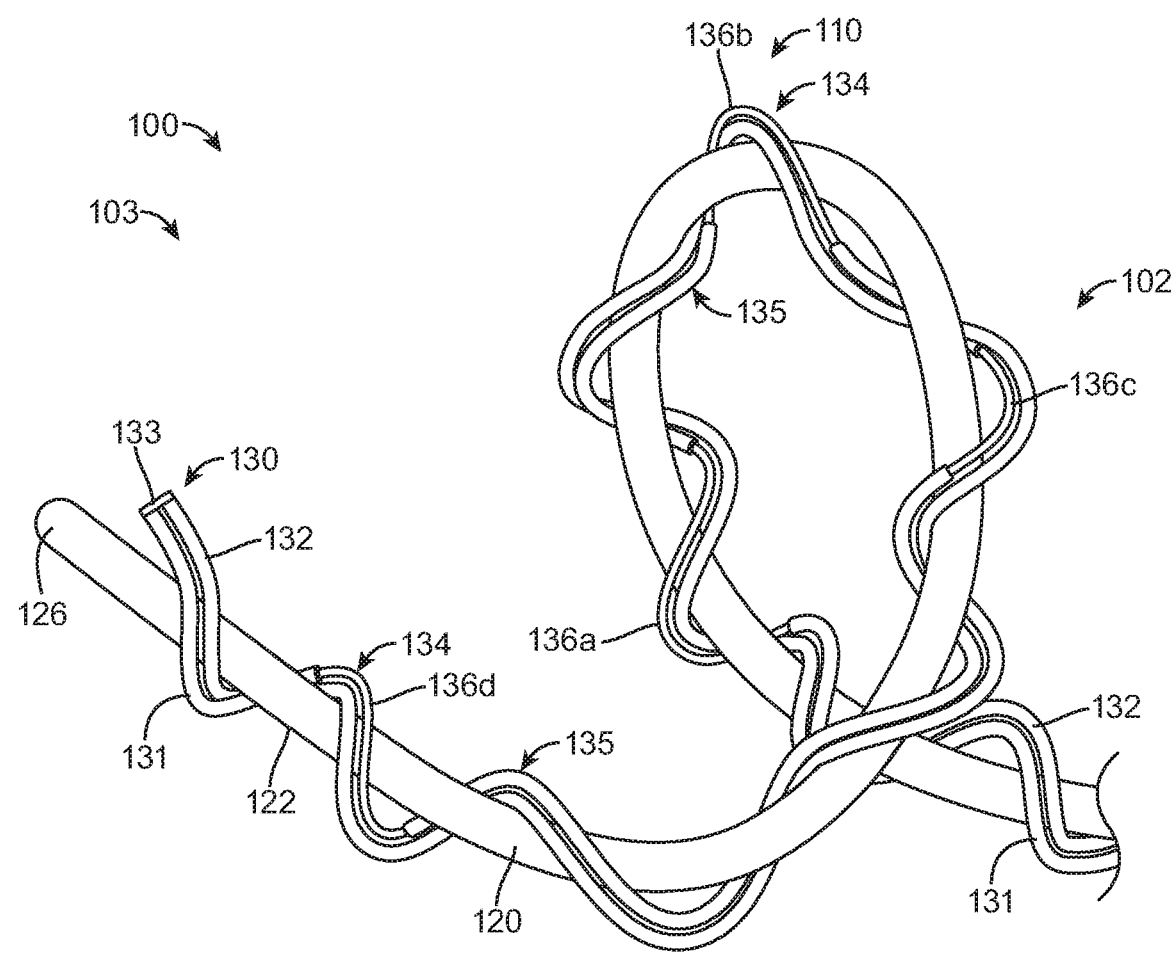
FIG. 1C is a perspective view of the distal portion of the catheter apparatus of FIG. 1B in a deployed state (e.g., expanded configuration) in accordance with an embodiment of the present technology.

FIGS. 1A and 1B illustrate assembly stages following steps in a method of forming a catheter apparatus 100 ("catheter 100") having a therapeutic assembly 110 in a distal portion 102 of the catheter 100 for therapeutically modulating sympathetic nerves in a patient in accordance with an embodiment of the present technology. FIG. 1C is a perspective view of the distal portion 102 of the catheter 100 of FIG. 1B in a deployed state 103 (e.g., expanded configuration). Referring to FIGS. 1A-1C together, the distal portion 102 includes an elongated tubular shaft 120, and the therapeutic assembly 110 can include the shaft 120 and a thermocouple assembly 130 positioned along the shaft 120. The therapeutic assembly 110 can be transformed or actuated between a delivery state 101 (e.g., a low-profile or collapsed configuration, FIG. 1B) and the deployed state 103 (e.g., a radially expanded, generally spiral configuration, FIG. 1C) in which the therapeutic assembly 110 is configured to contact a wall of a blood vessel (e.g., a renal blood vessel).

Referring back to FIGS. 1A and 1B, the therapeutic assembly 110 of the catheter 100 is shown in various stages of assembly for forming the catheter apparatus 100 in a delivery state 101 (e.g., low-profile or collapsed configuration) outside of a patient. As best seen in FIG. 1A, the shaft 120 can include a flexible tube 122 and a pre-shaped spiral/helical control member 124 within the tube 122. The flexible tube 122 may be composed of a polymer material such as: polyamide; polyimide; polyether block amide copolymer sold under the trademark PEBAX; polyethylene terephthalate (PET); polypropylene; aliphatic, polycarbonate-based thermoplastic polyurethane sold under the trademark CARBOTHANE; or a polyether ether ketone (PEEK) polymer that provides the desired flexibility. In other embodiments, however, the tube 122 may be composed of other suitable materials.

As mentioned above, the pre-shaped control member 124 may be used to provide a spiral/helical shape to the shaft 120 in the distal portion 102 of the catheter 100. In one embodiment, the control member 124 can be a tubular structure comprising a nitinol multifilar stranded wire with a lumen therethrough and sold under the trademark HELICAL HOLLOW STRAND (HHS), and commercially available from Fort Wayne Metals of Fort Wayne, Ind. The tubular control member 124 may be formed from a variety of different types of materials, may be arranged in a single or dual-layer configuration, and may be manufactured with a selected tension, compression, torque and pitch direction. The HHS material, for example, may be cut using a laser, electrical discharge machining (EDM), electrochemical grinding (ECG), or other suitable means to achieve a desired finished component length and geometry.

Forming the control member 124 of Nitinol multifilar stranded wire(s) or other similar materials is expected to provide a desired level of support and rigidity to the therapeutic assembly 110 without additional reinforcement wire(s) or other reinforcement features within the shaft 120. This feature is expected to reduce the number of manufacturing processes required to form the catheter 100 and reduce the number of materials required for the device. In one embodiment, the control member 124 and inner wall of the tube 122 can be in intimate contact with little or no space between the control member 124 and the tube 122. In some embodiments, for example, the tube 122 can have a larger diameter than the control member 124 prior to assembly such that applying hot air to the tube 122 during the manufacturing process shrinks the tube onto the control member 124, as will be understood by those familiar with the ordinary use of shrink tubing materials. This feature is expected to inhibit or eliminate wrinkles or kinks that might occur in the tube 122 as the therapeutic assembly 110 transforms from the relatively straight delivery state 101 to the deployed, generally spiral state 103 (FIG. 1C).

In other embodiments, the control member 124 and/or other components of the shaft 120 (e.g., in the distal portion 102 of the catheter 100) may be composed of different materials and/or have a different arrangement. For example, the control member 124 may be formed from other suitable shape memory materials (e.g., nickel-titanium (Nitinol), wire or tubing besides HHS, shape memory polymers, electro-active polymers) that are pre-formed or pre-shaped into the desired deployed state. Alternatively, the control member 124 may be formed from multiple materials such as a composite of one or more polymers and metals.

FIG. 1A illustrates a stage in the method of forming the therapeutic assembly 110 in the distal portion 102 of the catheter 100 after the thermocouple assembly 130 has been aligned with and positioned alongside the shaft 120. In the embodiment shown in FIG. 1A, the thermocouple assembly 130 includes a conductive first wire 131 and a second wire 132 joined at a junction 133 at least proximate to the shaft 120. The first and second wires 131, 132 can be dissimilar metals. In some embodiments, the first and second wires 131, 132 can be at least partially covered by an insulative cover 137, such as compacted mineral insulation and an outer sheath, or other appropriate conductive wire insulation known in the art. In one embodiment, the conductive first wire 131 can include an insulated energy delivery or transmitting wire that can relay and/or transmit an energy signal from an energy source (not shown), such as an RF energy generator located outside of the patient. In one embodiment, RF signals can be transmitted along a length of the conductive first wire 131 to the therapeutic assembly 110.

FIG. 1A also shows a stage in the method after selected portions of the insulating cover 137 have been removed from along the conductive first wire 131 to form a plurality of exposed regions 134 (e.g., uninsulated regions) separated from each other by insulated regions 135 along a portion of the first wire 131 proximate the shaft 120 (e.g., in the distal portion 102 of the catheter 100). The exposed regions 134 of the conductive first wire 131 can define a plurality of energy delivery portions 136a-136d (referred to collectively as energy delivery portions 136) configured to deliver electrical energy (e.g., RF energy, pulsed energy, etc.) to target tissue. In this embodiment, the energy delivery portions 136 (e.g., the exposed regions 134) are along the same conductive path and, accordingly, commonly connected to an energy source. The thermocouple assembly 130 can include more than one exposed region 134 along the first wire 131. For example the thermocouple assembly 130 can include between 2 and about 8 exposed regions 134 along the first wire 131, or between 2 and about 6 exposed regions 134, or between 2 and about 4 exposed regions 134, or about 4 exposed regions 134. In some embodiments, the energy delivery portions 136a-136d may be equally spaced apart along a length $L_1$ of the therapeutic assembly 110. In other embodiments, however, the number, size and arrangement (e.g., spacing) of the energy delivery portions 136 may vary. For example, a first energy delivery portion 136a may have a first size (e.g., a first length) and a second energy delivery portion 136b may have a second size (e.g., a second length) different than the first size, and/or first and second energy delivery portions 136a and 136b may be spaced apart by a different distance than second and third energy delivery portions 136b and 136c.

The thermocouple assembly 130 can also include the second wire 132, which can be a wire that is at least insulated along the shaft 120. The second wire 132 can run parallel to the first wire 131 and can be electrically coupled to the junction 133. The first wire 131 and the second wire 132 include dissimilar metals such that the electric potential between the two wires 131, 132 formed at the junction 133 relates to a temperature reading at the junction (e.g., at the therapeutic assembly 110). In one embodiment, the first wire 131 comprises a conductive material, such as nickel, silver, or in another embodiment, silver-coated nickel. In some embodiments, the conductive first wire 131 and/or the exposed regions 134 of the first wire 131 can be coated with a biocompatible conductive material (not shown), such as gold or platinum. In some embodiments, a non-biocompatible material (e.g., copper) may be used, for example in a Type T thermocouple or other non-biocompatible thermocouple, along with a biocompatible conductive material such as gold or platinum (e.g., coating for the non-biocompatible materials). Biocompatible materials and/or coatings, however, can be used with any of the thermocouple assemblies 130 described herein. Additional intermediate bonding materials (e.g., tantalum, titanium, etc.) may also be included. In various embodiments, the second wire 132 can be an insulated constantan wire. In a specific embodiment, the thermocouple assembly 130 can be a Type T thermocouple and the first wire 131 can be copper (e.g., gold or platinum coated copper) and the second wire 132 can be constantan. In this example, the thermocouple assembly 130 can measure temperatures in the temperature range of about −200° C. to about 350° C.

FIG. 1B illustrates a stage in the method after the thermocouple assembly 130 has been helically/spirally positioned about the shaft 120 (e.g., in the distal portion 102 of the catheter 100). In this embodiment, the shaft 120 supports the thermocouple assembly 130 about an outer circumference of the distal portion of the catheter 100 and along a length $L_1$ of the therapeutic assembly 110. As shown in FIG. 1B, the thermocouple assembly 130 can be helically positioned (e.g., wound, wrapped, arranged, etc.) about the shaft 120 (e.g., in the distal portion 102 of the catheter 100) while the therapeutic assembly 110 is in the delivery state 101. In one example, the thermocouple assembly 130 can be positioned about the shaft 120 to create a helical shape; however, a variety of helical or non-helical arrangements are suitable for positioning the thermocouple assembly 130 on or about the shaft 120. In some embodiments, the thermocouple assembly 130 may have a pitch of about 1 mm to 12 mm. In other embodiments, however, the thermocouple assembly 130 may have different dimensions.

The thermocouple assembly 130 may be coupled or attached to the shaft 120 (e.g., attached to the flexible tube 122) at one or more locations along the shaft 120 using adhesives (e.g., thermal bonds), fasteners, and/or other suitable attachment mechanisms known in the art (e.g., clips, ties, staples, collars, etc.). In one embodiment, the therapeutic assembly 110 can include proximal and distal connectors or retainers (not shown), such as collars or other suitable fasteners to which proximal and distal portions of the thermocouple assembly 130, respectively, may be attached. In such arrangements, the first and second wires 131, 132 can be helically positioned around the shaft 120 between the proximal and distal connectors (not shown). In various arrangements, such connectors may be attached over select portions of the shaft 120, thereby coupling the thermocouple assembly 130 to the shaft 120. The connectors can be attached to the shaft 120, for example, using thermal bonds, adhesives, interlocking surfaces (e.g., threads), friction fit, snap fit, suction, and/or other suitable attachment mechanisms, or the connectors can be formed integrally with the thermocouple assembly 130 and/or the shaft 120. In other embodiments, the therapeutic assembly 110 does not include additional connectors or attachment means, but can be retained against the shaft 120 with a guide sheath or loading tool (not shown) that is moved over the length $L_1$ of the therapeutic assembly 110 during advancement and retrieval.

The junction 133 of the thermocouple assembly 130 can be positioned at a distal end of the therapeutic assembly 110 which may or may not be a distal end 126 of the shaft 120 (FIGS. 1B and 1C). In one example, the catheter 100 terminates at an atraumatic tip 128 at the distal end 126 of the shaft 120 (FIG. 1B). The atraumatic tip 128 can be a flexible curved tip. In one embodiment, the atraumatic tip 128 may have a distal opening (not shown) for accommodating a guide wire (not shown) that directs the guide wire away from the wall of the artery when the therapeutic assembly 110 is in the pre-set deployed state 103 (FIG. 1C). The curvature of the tip 128 can be varied depending upon the particular sizing/configuration of the therapeutic assembly 110. In some embodiments, the tip 128 may also comprise one or more radiopaque markers (not shown) and/or one or more sensors (not shown). In one embodiment, the tip 128 can be part of (e.g., an extension of or integral with) the shaft 120. In one example, the flexible tip 128 can be a more flexible tapered portion (e.g., about 5 to about 7 mm) of the distal end 126 of the shaft 120. Such an arrangement can be suitable for guidewire delivery of the therapeutic assembly 110 to the target treatment site. In another embodiment, the tip 128 can be a separate component that may be affixed to the distal end 126 of the shaft 120 via adhesive, crimping, over-molding, or other suitable techniques. The tip 128 can be made from a polymer material (e.g., a polyether block amide copolymer sold under the trademark PEBAX, or a thermoplastic polyether urethane material sold under the trademarks ELASTHANE or PELLETHANE), or other suitable materials having the desired properties, including a selected durometer. In other embodiments, the tip 128 may be formed from different material(s) and/or have a different arrangement.

FIG. 1C is a perspective view of the distal portion 102 of the catheter 100 of FIG. 1B in the deployed state 103 (e.g., expanded configuration) in accordance with an embodiment of the present technology. In this embodiment, the control member 124 (FIG. 1A) has a pre-set spiral/helical configuration that defines the deployed state 103 of the therapeutic assembly 110 such that the energy delivery portions 136a-136d of the thermocouple assembly 130 are offset from each other (e.g., both angularly and circumferentially offset relative to a longitudinal axis of the artery and/or angularly offset from each other along an axis of the shaft 120 when the thermocouple assembly 130 is in the deployed configuration). This configuration can provide stable apposition of the energy delivery portions 136a-136d with an inner surface of a wall of the artery (not shown) for treatment. As shown in FIG. 1C, the exposed regions 134 along the first wire 131 of the thermocouple assembly 130 are spaced apart from each other. However, because the insulated regions 134 expose portions of a single first wire 131, the energy delivery portions 136a-136d defined by the exposed regions 134 are in electrical communication with each other (e.g., commonly connected to an energy source).

Once deployed, the therapeutic assembly 110 can deliver neuromodulating energy from a power source (not shown) and through the thermocouple assembly 130 (e.g., through the first wire 131) to the energy delivery portions 136a-136d. The purposeful application of energy (e.g., electrical energy such as RF energy and pulsed energy) to tissue at the treatment location within the artery (e.g., renal artery) can induce one or more desired effects at the treatment location, e.g., broadly across the treatment location or at localized regions of the treatment location. In one embodiment, an RF energy field can be delivered to the target nerves adjacent the wall of the artery via the energy delivery portions 136a-136d. In the illustrated embodiment, the energy delivery portions 136a-136 are spaced apart both circumferentially and longitudinally along the wall of the interior lumen of the artery when the therapeutic assembly 110 is in the deployed state 103. Accordingly, application of energy via the energy delivery portions 136a-136d can result in a plurality of discontinuous lesions along the wall of the interior lumen of the artery. Temperature of the target tissue proximate the therapeutic assembly 110 can be measured and monitored by the thermocouple assembly 130 at the junction 133.

Referring to FIGS. 1B and 1C together, and as described in more detail below with reference to FIG. 5, the catheter 100 may be configured for guidewire based delivery (e.g., over-the-wire ("OTW") delivery, rapid exchange ("RX") delivery) from an access site in which a guide wire (not shown) is initially inserted to a treatment site (e.g., within a renal artery), and the catheter 100 is advanced over the guide wire. For example, the guide wire may be either inserted into or at least partially withdrawn from the shaft 120 (e.g., in the distal portion 102 of the catheter 100) to transform the therapeutic assembly 110 between the delivery state 101 (FIG. 1B) and the deployed state 103 (FIG. 1C). For example, a guide wire (not shown) extending through at least a portion of the length of the catheter 100 (e.g., through a lumen defined by the shaft 120) may be configured to straighten the pre-shaped spiral/helical control member 124 of the catheter 100 during delivery, and the guide wire may be at least partially withdrawn or slideably moved relative to the shaft 120 to allow the therapeutic assembly 110 to transform to the deployed state 103 (FIG. 1C).

Figure 1D:
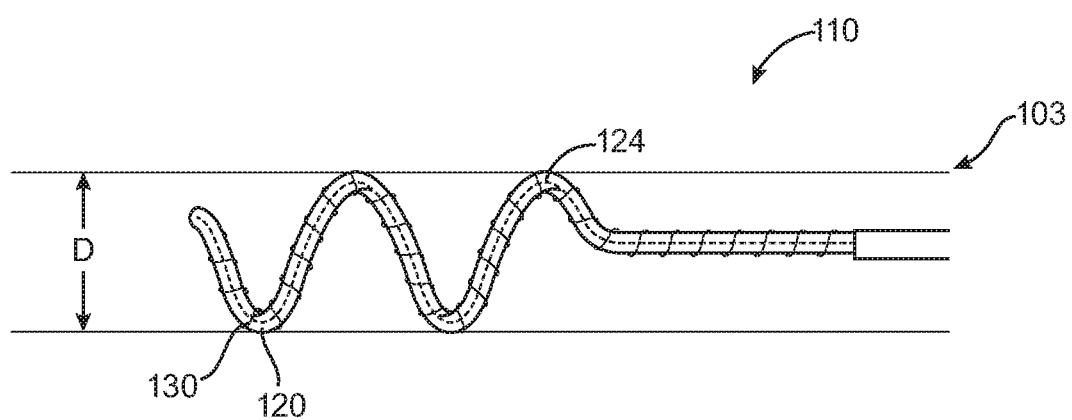
FIG. 1D is a partially schematic side view of the distal portion of the catheter apparatus of FIG. 1C in the deployed state.

As best seen in FIG. 1D, in its deployed state 103, the spiral/helical therapeutic assembly 110 may have an outer diameter D of between about 4 mm and about 9 mm to accommodate, for example, blood vessel sizes having diameters in range of about 3 mm to about 8 mm. As noted above, the control member 124 (shown schematically as a broken line) is itself pre-set into a spiral/helical shape. The dimensions of the spiral/helical shape of the control member 124 may be substantially the same as those of the spiral/helical therapeutic assembly 110.

In the embodiment illustrated in FIGS. 1A-1C, the therapeutic assembly 110 does not include dedicated electrodes separate from the exposed portions 134 of the first wire 131 of the thermocouple assembly 130, or any other conductors or bifilar wires that extend through the lumen or along the surface of the flexible tube 122 or elsewhere along the shaft 120. Instead, the embodiment illustrated in FIGS. 1A-1C is configured to deliver neuromodulating energy to target tissue via the thermocouple assembly 130. An advantage to this embodiment is that the additional manufacturing costs associated with adding separate electrodes and associated wiring of each individual electrode can be avoided while still delivering energy (e.g., RF energy) in suitable frequencies for desirably affecting the target tissue. In other embodiments not shown, however, one or more separate electrodes can be included in the therapeutic assembly 110. For example, a separately wired electrode can be positioned at any location along the length $L_1$ of the therapeutic assembly 110 to deliver the same or a different form of energy as that of the energy delivery portions 136 of the thermocouple assembly 130.

Figure 2A:
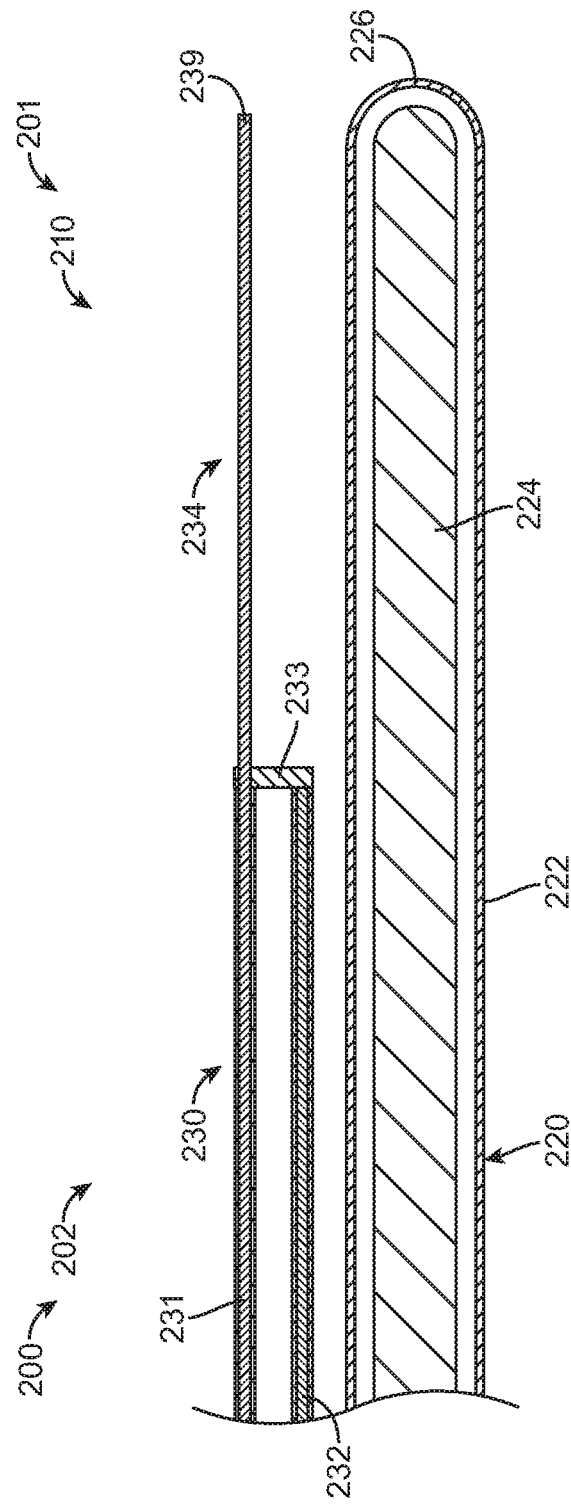
FIG. 2A is an enlarged cross-sectional side view illustrating a therapeutic assembly of a neuromodulation catheter apparatus following a step in a process for assembling the therapeutic assembly from an unassembled state outside a patient in accordance with another embodiment of the present technology.
Figure 2B:
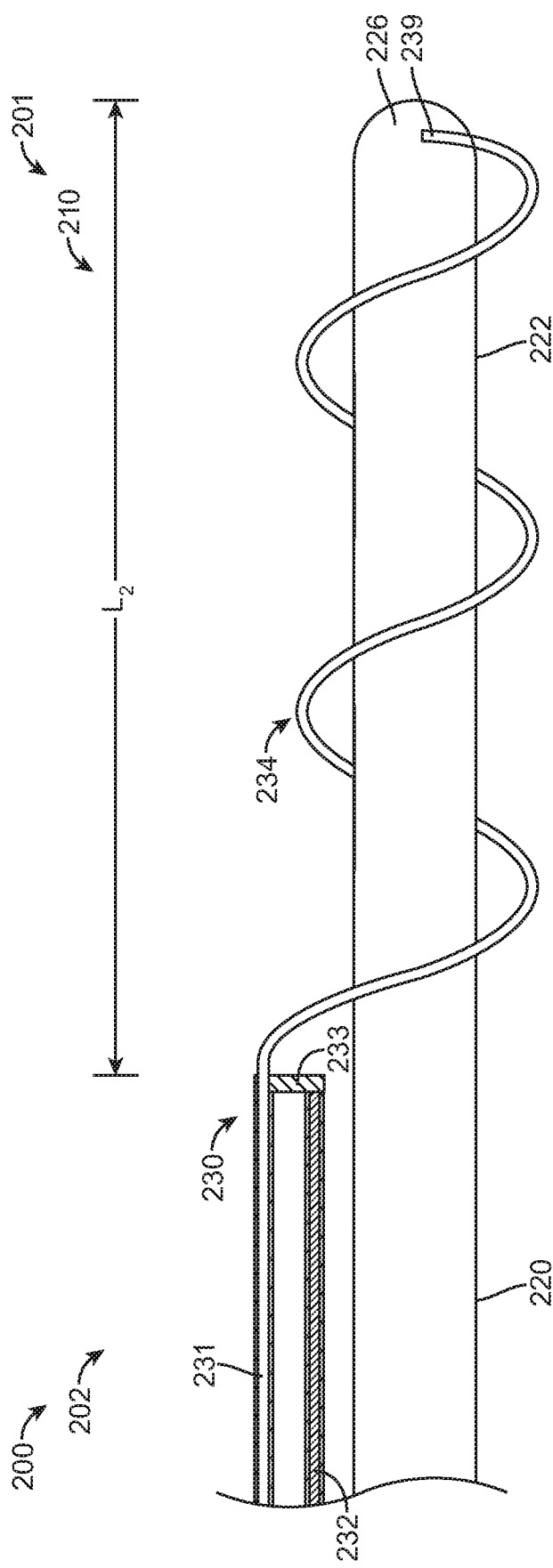
FIGS. 2B and 2C are enlarged, partial cross-sectional side views illustrating assembly stages following additional steps in the process for making the therapeutic assembly of the catheter apparatus shown in FIG. 2A in accordance with embodiments of the present technology.
Figure 2C:
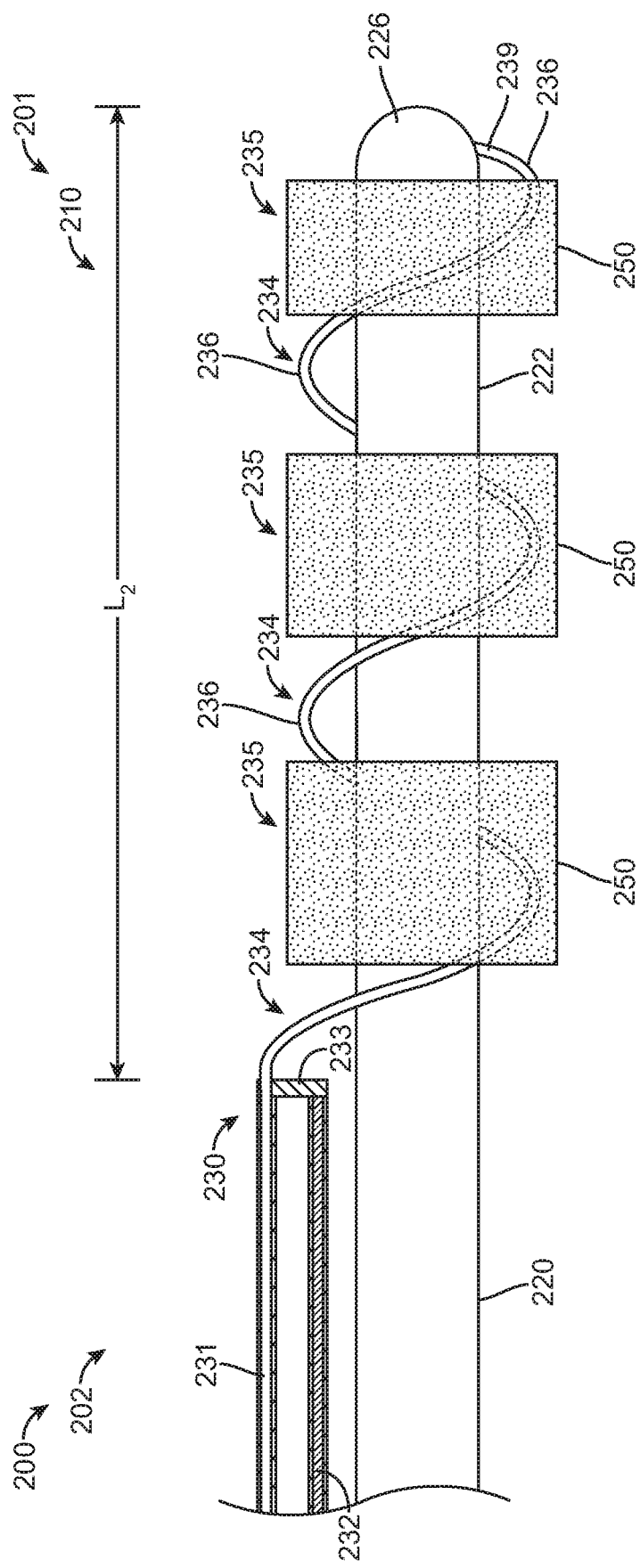
Figure 2D:
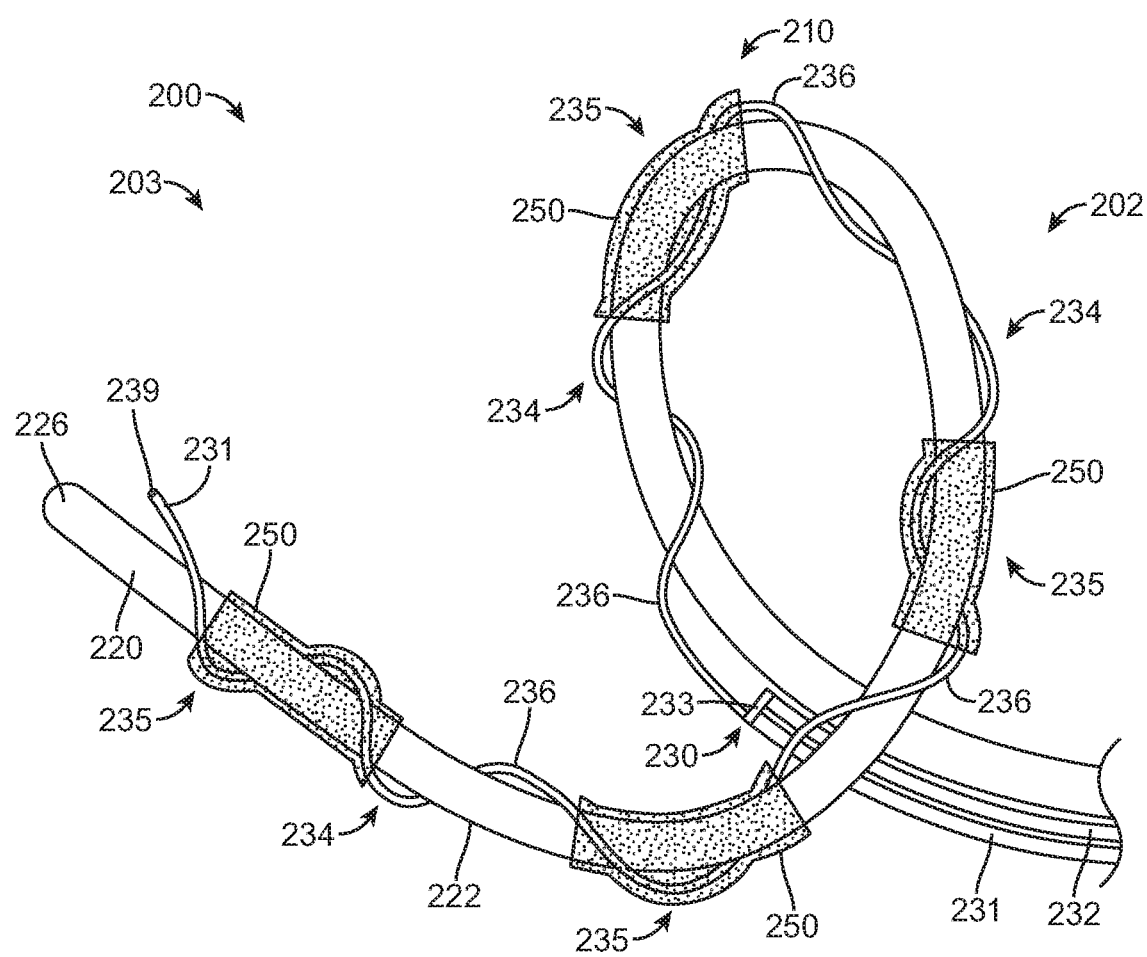
FIG. 2D is a perspective view of the distal portion of the catheter apparatus of FIG. 2C in a deployed state (e.g., expanded configuration) in accordance with an embodiment of the present technology.

FIGS. 2A-2C illustrate assembly stages following steps in a method of forming a catheter apparatus 200 ("catheter 200") having a therapeutic assembly 210 in a distal portion 202 of the catheter 200 for therapeutically modulating sympathetic nerves in accordance with another embodiment of the present technology. FIG. 2D is a perspective view of the distal portion 202 of the catheter 200 of FIG. 2C in a deployed state 203 (e.g., expanded configuration). Referring to FIGS. 2A-2D together, the catheter 200 includes features generally similar to the features of the catheter 100 described above with reference to FIGS. 1A-1C. For example, the distal portion 202 of the catheter 100 includes an elongated tubular shaft 220, and includes a therapeutic assembly 210 having a thermocouple assembly 230 positioned about the shaft 220. However, in the embodiment shown in FIGS. 2A-2D, the thermocouple assembly 230 includes a junction 233 positioned proximal of a distal end 226 of the shaft 220 and includes a single exposed region 234 (e.g., an uninsulated region) of a first wire 231 that extends distal to the junction 233 and toward the distal end 226.

FIG. 2A is an enlarged cross-sectional side view of the therapeutic assembly 210 in a partially assembled state illustrating a stage in the assembly method after the thermocouple assembly 230 has been aligned with and positioned alongside the shaft 220 (e.g., in a distal portion 202 of the catheter 200). Similar to the embodiment described above with respect to FIGS. 1A-1C, the shaft 220 can include a flexible tube 222 and a pre-shaped spiral/helical control member 224 within the tube 222. FIG. 2A also illustrates a step in the process of arranging the thermocouple assembly 230 after an insulating portion has been removed from along the conductive first wire 231 in the region 234 between the junction 233 and an end 239 of the first wire 231. The thermocouple assembly 230 also includes an insulated second wire 232 that terminates at the junction 233.

FIGS. 2B and 2C are enlarged, partial cross-sectional side views illustrating assembly stages following additional steps in the process for arranging the therapeutic assembly 210 of the catheter 200 shown in FIG. 2A. For example, FIG. 2B illustrates a partially assembled stage in the process after the exposed region 234 of the first wire 231 has been helically positioned about the shaft 220. In this embodiment, the shaft 220 supports the exposed region 234 about an outer circumference of the distal portion of the shaft 220 and along a length $L_2$ of the therapeutic assembly 210. As shown in FIG. 2B, the exposed region 234 of the first wire 231 can be helically positioned (e.g., wound, wrapped, arranged, etc.) about the shaft 220 (e.g., in a distal portion 202 of the catheter 200) while the therapeutic assembly 210 is in the delivery state 201. In one example, the thermocouple assembly 230 can be positioned about the shaft 220 to create a helical shape. A variety of helical or non-helical arrangements, however, are suitable for positioning the thermocouple assembly 230 on or about the shaft 220.

FIG. 2C illustrates a final assembly stage in the process after disposing one or more sleeves 250 composed of insulative material about portions of the first wire 231 and the shaft 220 (e.g., in a distal portion 202 of the catheter 200). The catheter 200 is in a delivery state 201 (e.g., low profile or collapsed configuration) in FIG. 2C. The one or more sleeves 250 can be placed along the therapeutic assembly 210 in positions aligned with the exposed region 234 of the first wire 231 to effectively disrupt the exposed region 234. The portions of the first wire 231 that remain exposed (e.g., not covered by the sleeves 250) can define a plurality of energy delivery portions 236, which can deliver or otherwise transmit electrical energy (e.g., RF energy, pulsed energy, etc.) to target tissue in a manner similar to the energy delivery portions 136 described above with respect to FIGS. 1A-1C. In some embodiments, the sleeves 250 may be equally spaced apart along the length $L_2$ of the therapeutic assembly 210 to define the plurality of energy delivery portions 236. In some embodiments, the number of energy delivery portions 236 can be four; however, in other embodiments, the number and arrangement of the energy delivery portions 236 may vary.

In one embodiment, the sleeves 250 can be a flexible and insulative material such as polyethylene terephthalate (PET) heat shrink tubing or other shrink tubing materials known in the art. In other embodiments, the sleeves 250 can be composed of other polymer materials with or without additional insulative layers or materials. For example, the sleeves 250 may comprise one or more of the following materials: polyamide; polyimide; polyether block amide copolymer sold under the trademark PEBAX; polypropylene; aliphatic, polycarbonate-based thermoplastic polyurethane sold under the trademark CARBOTHANE; or a polyether ether ketone (PEEK) polymer that provides the desired material properties. In other embodiments, however, the sleeves 250 may be composed of other or additional suitable materials.

In some embodiments, the sleeves 250 are portions of tubing suitable to place over the distal end 226 of the shaft 220 and positioned at a further proximal site along the therapeutic assembly 210. The sleeves 250 can be heat shrunk around the first wire 231 and the shaft 220 using known processes in the art, such that the exposed region 234 of the first wire 231 (e.g., the portion of the wire 231 after the insulating portion has been removed) is held in place (e.g., helically positioned about the shaft 220) and the sleeves 250 provide intermittently positioned insulated regions 235 along the first wire 231 to define the plurality of energy delivery portions 236. In one embodiment, adhesive (not shown) can be placed between an inner surface of the sleeves 250 and the shaft 220 (e.g., the flexible tube 222) to prevent blood from collecting and/or clotting between the sleeves 250 and the shaft 220. In other embodiments, the sleeves 250 can include material that is wrapped about the shaft 220 and secured into position using known mechanical fastening components or adhesive.

FIG. 2D is a perspective view of the distal portion 202 of the catheter 200 of FIG. 2C in a deployed state 203 (e.g., expanded configuration) in accordance with an embodiment of the present technology. As previously described, the control member 224 (FIG. 2A) has a pre-set spiral/helical configuration that can define the deployed state 203 of the therapeutic assembly 210 such that the energy delivery portions 236 of the thermocouple assembly 230 are offset from each other (e.g., both angularly and circumferentially offset relative to a longitudinal axis of the artery and/or angularly offset from each other along an axis of the shaft 220 when the thermocouple assembly 210 is in the deployed configuration) and may be positioned in stable apposition with an inner surface of a wall of the artery (not shown) for treatment. Additionally, the energy delivery portions 236 along the first wire 231 are defined by the spacing between the sleeves 250 and are spaced apart from each other when the therapeutic assembly 210 is in the deployed state 203. However, the energy delivery portions 236 are commonly connected to each other. Once deployed, the therapeutic assembly 210 (like the therapeutic assembly 110 shown in FIG. 1C) can deliver neuromodulating energy from a power source (not shown) and through the thermocouple assembly 230 (e.g., through the first wire 231) to the target tissue via the energy delivery portions 236.

Figure 3:
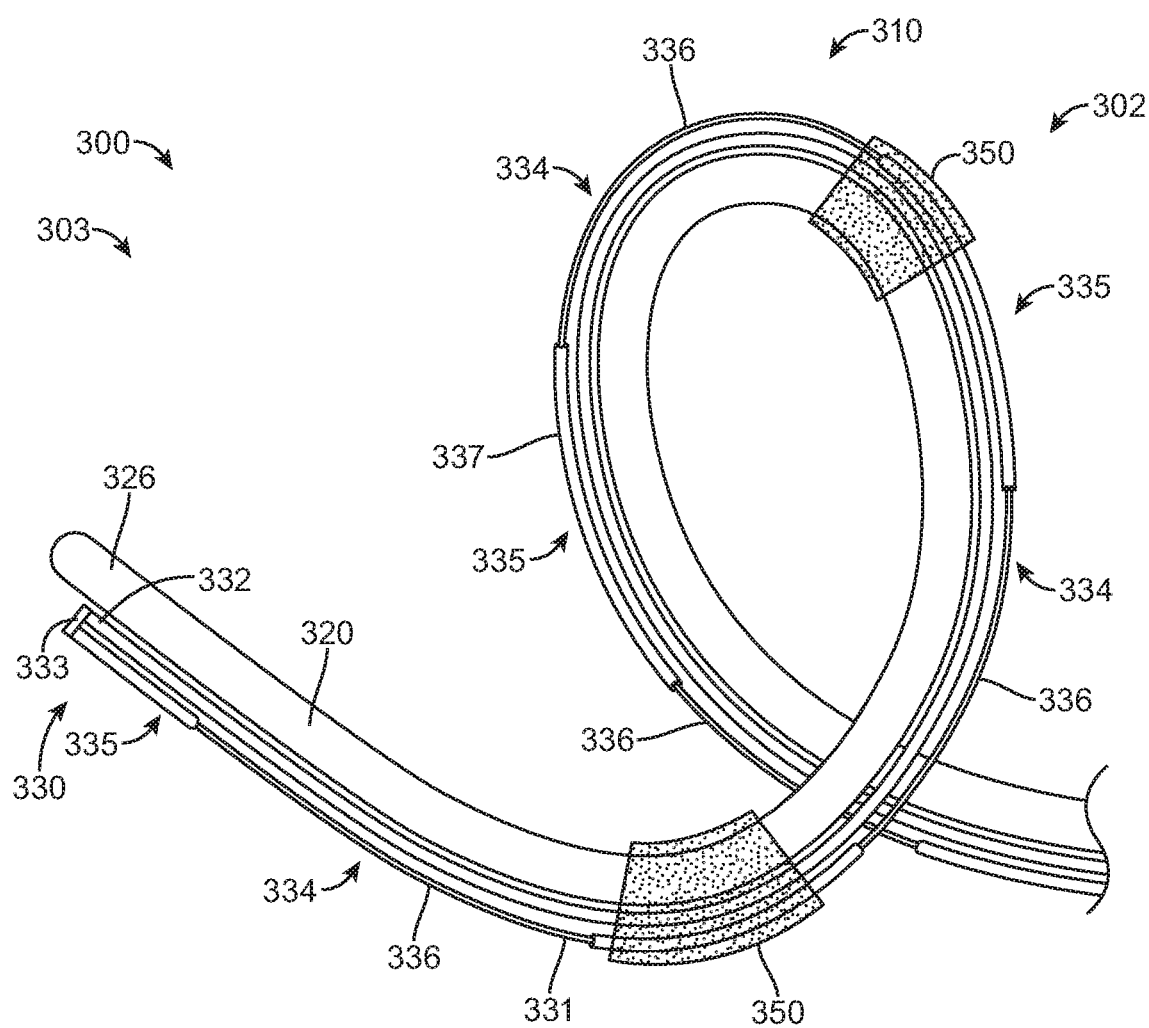
FIG. 3 is a perspective view of a distal portion of a catheter having a therapeutic assembly or treatment section in a deployed state (e.g., expanded configuration) in accordance with a further embodiment of the present technology.

FIG. 3 illustrates a distal portion 302 of a catheter apparatus 300 ("catheter 300") having a therapeutic assembly 310 or treatment section in a deployed state 303 (e.g., expanded configuration) in accordance with a further embodiment of the present technology. FIG. 3 is a perspective view of the distal portion 302 that includes features generally similar to the features of the catheters 100, 200 described above with reference to FIGS. 1A-2D. For example, the distal portion 302 of the catheter 100 includes an elongated tubular shaft 320, and includes the therapeutic assembly 310 having a thermocouple assembly 330 positioned along the shaft 320. However, in the embodiment shown in FIG. 3, the thermocouple assembly 330 is not helically positioned about the shaft 320; rather, the thermocouple assembly 330 is positioned longitudinally along the shaft 320 (e.g., in the distal portion 302 of the shaft 320). The embodiment illustrated in FIG. 3 shows the thermocouple assembly 330 secured to the shaft 320 with one or more sleeves 350, however, one of ordinary skill in the art will recognize that the thermocouple assembly 330 can be secured into position using other known mechanical fastening components (e.g., clips, collars, etc.) or adhesive.

The embodiment illustrated in FIG. 3 includes the thermocouple assembly 330 having an arrangement similar to the thermocouple assembly arrangement shown in FIG. 1A. For example, the thermocouple assembly 330 includes a conductive first wire 331 and a second wire 332 joined at a junction 333 at least proximate to a distal end 326 of the shaft 320. As described above, the first and second wires 331, 332 can be dissimilar metals and can include an insulative cover 337 over the wires, such as compacted mineral insulation and an outer sheath, or other appropriate conductive wire insulation known in the art. The conductive first wire 331 can relay and/or transmit an energy signal from an energy generating source (not shown), such as an RF energy generator located outside of the patient, and along a length of the conductive first wire 331 to the therapeutic assembly 310. Similar to the thermocouple assembly 130 shown in FIG. 1A, the thermocouple assembly 330 includes a plurality of exposed regions 334 (e.g., uninsulated regions) and insulated regions 335 along a portion of the first wire 331 to define a plurality of energy delivery portions 336 at the exposed regions 334. In this embodiment, the energy delivery portions 336 (e.g., the exposed regions 334) are along the same conductive path and, accordingly, commonly connected with each other.

In a pre-deployed configuration of the therapeutic assembly 310, the sleeves 350 can be positioned along the therapeutic assembly 310 to secure the thermocouple assembly 330 to the shaft 320. In this embodiment, the sleeves 350 can be similar to the sleeves 250 described above with respect to FIGS. 2C and 2D, or in another embodiment, the sleeves 350 may not include insulative properties, but serve to couple the thermocouple assembly 330 to the support structure 321. In some embodiments of devices described herein, a sleeve can perform both functions. In a delivery state, the shaft 320 has a longitudinal axis or orientation, and the thermocouple assembly 330 extends at least generally parallel to the longitudinal axis of the shaft 320. When deployed, the therapeutic assembly 310 has a pre-set spiral/helical configuration that defines the deployed state 303 of the therapeutic assembly 310 such that the energy delivery portions 336 of the thermocouple assembly 330 are both longitudinally offset (e.g., along the therapeutic assembly 310) and angularly or circumferentially offset (e.g., as defined by the spiral configuration of the shaft 320) from each other relative to a longitudinal axis of the artery. Accordingly, the energy delivery portions 336 may be positioned in stable apposition with an inner surface of a wall of the artery (not shown) for treatment.

ADDITIONAL EMBODIMENTS

Features of the catheter device components described above and illustrated in FIGS. 1A-3 can be modified to form additional embodiments configured in accordance with the present technology. For example, the catheter 100 illustrated in FIGS. 1A-1C and other catheter apparatuses described above and illustrated in FIG. 2A without sleeves can include sleeves that provide additional coupling of the first and/or second thermocouple wires to the shaft and/or provide additional insulation in selected regions where the sleeves are positioned. Further modifications of the therapeutic assembly 210 illustrated in FIG. 2B can include securing the exposed region 234 of the first wire 231 with non-insulating mechanical components such that a continuous helical lesion (rather than discrete lesions formed in a helical pattern; FIGS. 2C and 2D) can be achieved. Similarly, the catheters described above and illustrated in FIGS. 1A-3 can include one or more control members configured to receive one or more control wires (e.g., pull wires). A control wire can be used, for example, to control (e.g., deflect, angle, position, or steer) a distal portion of the shaft, a thermocouple assembly, or another catheter device component from outside the vasculature.

Features of the catheter device components described above also can be interchanged to form additional embodiments of the present technology. For example, while FIG. 3 illustrates a therapeutic assembly having a non-helically positioned thermocouple assembly arrangement similar to the arrangement shown in FIG. 1A, another embodiment of a catheter in accordance with the present technology could include a therapeutic assembly having a non-helically positioned thermocouple assembly arrangement similar to the arrangement shown in FIG. 2A and including a plurality of insulative sleeves to define energy delivery portions. Additionally, the catheter apparatuses described above can also include additional thermocouple assemblies, electrode elements, wires, and energy delivery features positioned along the distal portion of the shaft.

Selected Examples of Neuromodulation Systems

Figure 4:
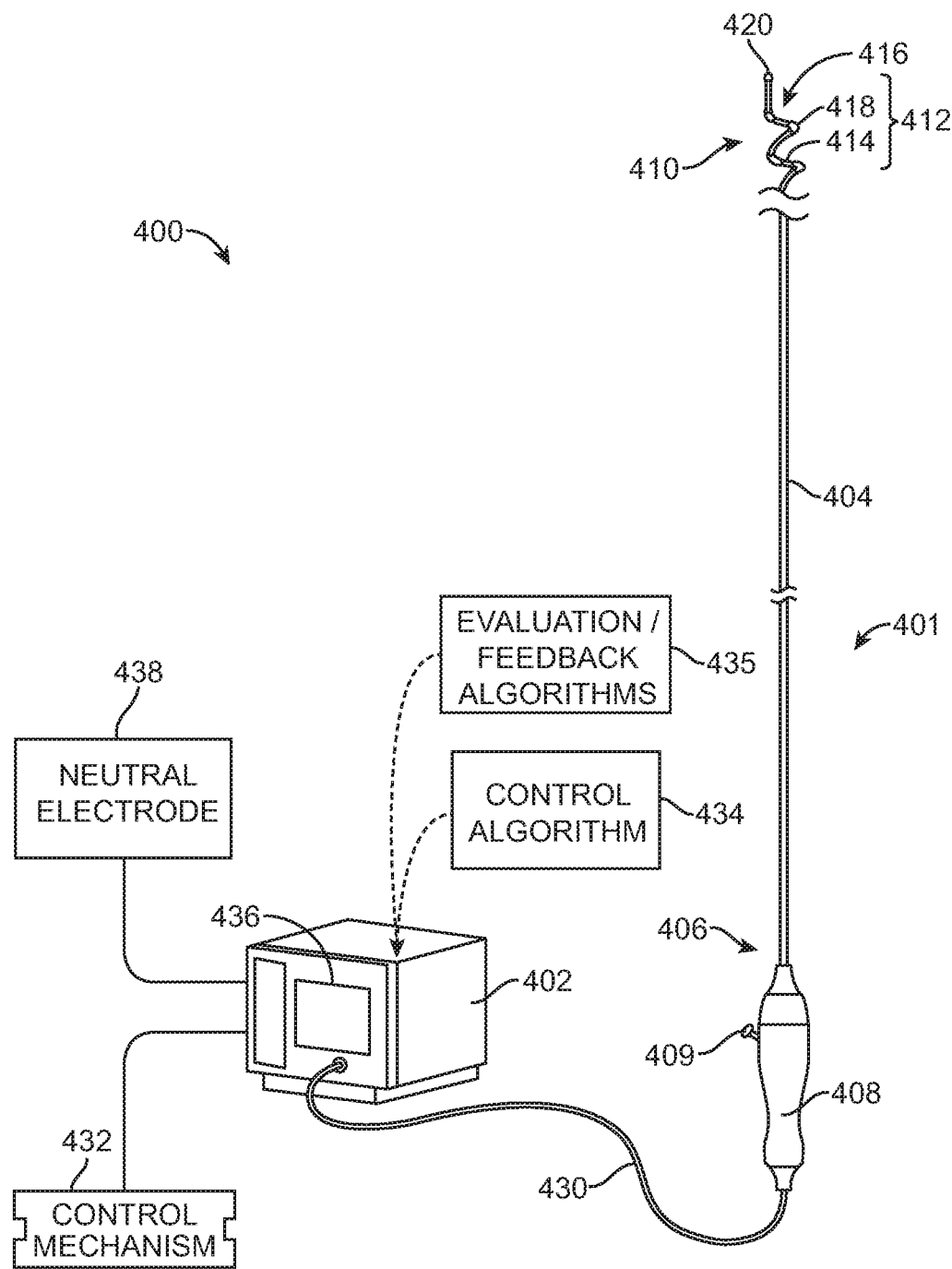
FIG. 4 is a partially schematic diagram of a neuromodulation system configured in accordance with an embodiment of the present technology.

FIG. 4 is a partially schematic illustration of a neuromodulation system 400 ("system 400") configured in accordance with an embodiment of the present technology. The system 400 includes an intravascular catheter 401, which in various embodiments can be any of the catheters 100 (FIGS. 1A-1C), 200 (FIGS. 2A-2D), 300 (FIG. 3), or another of the catheters described above, operably coupled to an energy source or energy generator 402 (e.g., an RF energy generator). The catheter 401 can include an elongated shaft 404 having a proximal portion 406, a handle 408 at a proximal region of the proximal portion 406, and a distal portion 410. The catheter 401 can further include a therapeutic assembly or treatment section 412 (shown schematically) at the distal portion 410 (e.g., attached to the distal portion 410, defining a section of the distal portion 410, etc.). As explained in further detail below, the therapeutic assembly 412 can include a support structure 414 and a thermocouple assembly 416 accompanying the support structure 414. As discussed above with respect to the therapeutic assemblies of the catheter devices illustrated in FIGS. 1A-3, the thermocouple assembly 416 can have an energy delivery wire (e.g., a first wire) having one or more exposed regions that define one or more energy delivery portions 418 along the length of the therapeutic assembly 412 and which is configured to be delivered to a target blood vessel (e.g., an artery, vein or ostium) in a low-profile configuration. As mentioned previously, targeted blood vessels can include, for example, a renal artery, an ovarian artery, testicular artery, external iliac artery, internal iliac artery, internal pudendal artery, uterine artery, celiac artery, superior mesenteric artery, hepatic artery, splenic artery, gastric artery, pancreatic artery, and/or associated arterial branches. One of ordinary skill in the art will recognize that the therapeutic assemblies and catheter devices described herein may be suitable for other blood vessel targets and conditions. Examples of suitable therapeutic and catheter delivery methods for targeting a variety of blood vessels and for therapeutic treatment of a variety of conditions are described, for example, in U.S. patent application Ser. No. 13/691,594 filed Nov. 30, 2012; U.S. patent application Ser. No. 13/691,556 filed Nov. 30, 2012; International Publication No. PCT/US2013/029690, filed Mar. 7, 2013; International Publication No. PCT/US2013/029547, filed Mar. 7, 2013; International Publication No. PCT/US2013/029679, filed Mar. 7, 2013; and International Publication No. PCT/US2013/029574, filed Mar. 7, 2013 each of which are incorporated herein by reference in their entireties.

Upon delivery to the target treatment site within the target blood vessel (e.g., renal blood vessel), the therapeutic assembly 412 is further configured to be deployed into an expanded state (e.g., a generally spiral/helical configuration, an expanded lasso or J-shaped configuration, etc.) for delivering energy at the treatment site and providing therapeutically-effective thermally-induced neuromodulation. Alternatively, the deployed state may be non-spiral provided that the deployed state provides adequate contact between energy delivery portions and the inner surface of the vessel wall. The therapeutic assembly 412 may be transformed between the delivery and deployed states using a variety of suitable mechanisms or techniques (e.g., self-expansion, remote actuation via an actuator, etc.). In a specific example, the neuromodulation assembly 412 may be placed or transformed into the deployed state or arrangement via remote actuation, e.g., via an actuator 409, such as a knob, pin, or lever carried by the handle 408. In another example, following placement of the therapeutic assembly at the treatment site, advancement of a pre-shaped or expandable element or wire (e.g., a Nitinol wire) into a lumen of the shaft or flexible tube can cause the therapeutic assembly to assume its deployed state.

The proximal end of the therapeutic assembly 412 is carried by or affixed to the distal portion 410 of the elongated shaft 404. A distal end of the therapeutic assembly 412 may terminate the catheter 401 with, for example, an atraumatic tip 420. In some embodiments, the distal end of the therapeutic assembly 412 may also be configured to engage another element of the system 400 or catheter 401. For example, the distal end of the therapeutic assembly 412 may define a passageway for receiving a guide wire (not shown) for delivery of the treatment device using OTW or rapid exchange ("RX") techniques. Further details regarding such arrangements are described below.

The catheter 401 can be electrically coupled to the energy source 402 via a cable 430, and the energy source 402 (e.g., an RF energy generator) can be configured to produce a selected modality and magnitude of energy for delivery to the treatment site via the thermocouple assembly's energy delivery portions 418 along the first wire. As described in greater detail below, thermocouple wires (not shown) can extend along the elongated shaft 404 or through a lumen in the shaft 404 to the therapeutic assembly 412 at the distal portion 410 of the elongated shaft 404 and transmit the treatment energy to the energy delivery portions 418 (e.g., the exposed regions of the energy delivering thermocouple wire). Accordingly, each energy delivery portion 418 can receive and deliver energy supplied by the single energy delivery wire within the thermocouple assembly 416 instead of each portion 418 having its own supply wire. The energy delivery portions 418 are positioned along the same electrical power wire or line, and accordingly, deliver power in a simultaneous fashion.

A control mechanism 432, such as a foot pedal or handheld remote control device, may be connected to the energy source 402 to allow the clinician to initiate, terminate and, optionally, adjust various operational characteristics of the energy source 402, including, but not limited to, power delivery. The remote control device (not shown) can be positioned in a sterile field and operably coupled to the thermocouple assembly, and specifically to the energy delivering thermocouple wire having the exposed (e.g., uninsulated) energy delivery portions 418, and can be configured to allow the clinician to activate and deactivate the energy delivery to the energy delivery portions 418. In other embodiments, the remote control device may be built into the handle assembly 408.

The energy source or energy generator 402 can be configured to deliver the treatment energy via an automated control algorithm 434 and/or under the control of a clinician. For example, the energy source 402 can include computing devices (e.g., personal computers, server computers, tablets, etc.) having processing circuitry (e.g., a microprocessor) that is configured to execute stored instructions relating to the control algorithm 434. In addition, the processing circuitry may be configured to execute one or more evaluation/feedback algorithms 435, which can be communicated to the clinician. For example, the energy source 402 can include a monitor or display 436 and/or associated features that are configured to provide visual, audio, or other indications of power levels, sensor data, and/or other feedback. The energy source 402 can also be configured to communicate the feedback and other information to another device, such as a monitor in a catheterization laboratory.

In some embodiments, the system 400 may be configured to provide delivery of a monopolar electric field via the energy delivery portions 418. In such embodiments, a neutral or dispersive electrode 438 may be electrically connected to the energy generator 402 and attached to the exterior of the patient (as shown in FIG. 5). The individual energy delivery portions (e.g., energy delivery portions 136, 236 and 336 from FIGS. 1A-3) are connected to the energy generator 402 and are sized and configured to contact an internal wall of the artery (e.g., the renal artery). In the illustrated embodiment, the energy delivery portions may be operated in a monopolar or unipolar mode. In this arrangement, a return path for the applied RF electric field is established, e.g., by the external dispersive electrode 438, also called an indifferent electrode or neutral electrode. The monopolar application of RF electric field energy serves to ohmically or resistively heat tissue in the vicinity of the electrode. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall. Alternatively, an RF electrical field may be delivered with an oscillating or pulsed intensity that does not thermally injure the tissue whereby neuromodulation in the targeted nerves is accomplished by electrical modification of the nerve signals.

The system 400 can also include one or more additional sensors (not shown) located proximate to or within the energy delivery portions 418. For example, the system 400 can include one or more other temperature sensors (e.g., one or more additional thermocouples, thermistors, etc.), impedance sensors, pressure sensors, optical sensors, flow sensors, and/or other suitable sensors connected to one or more supply wires (not shown) that transmit signals from the sensors and/or convey energy to the therapeutic assembly 412.

Figure 5:
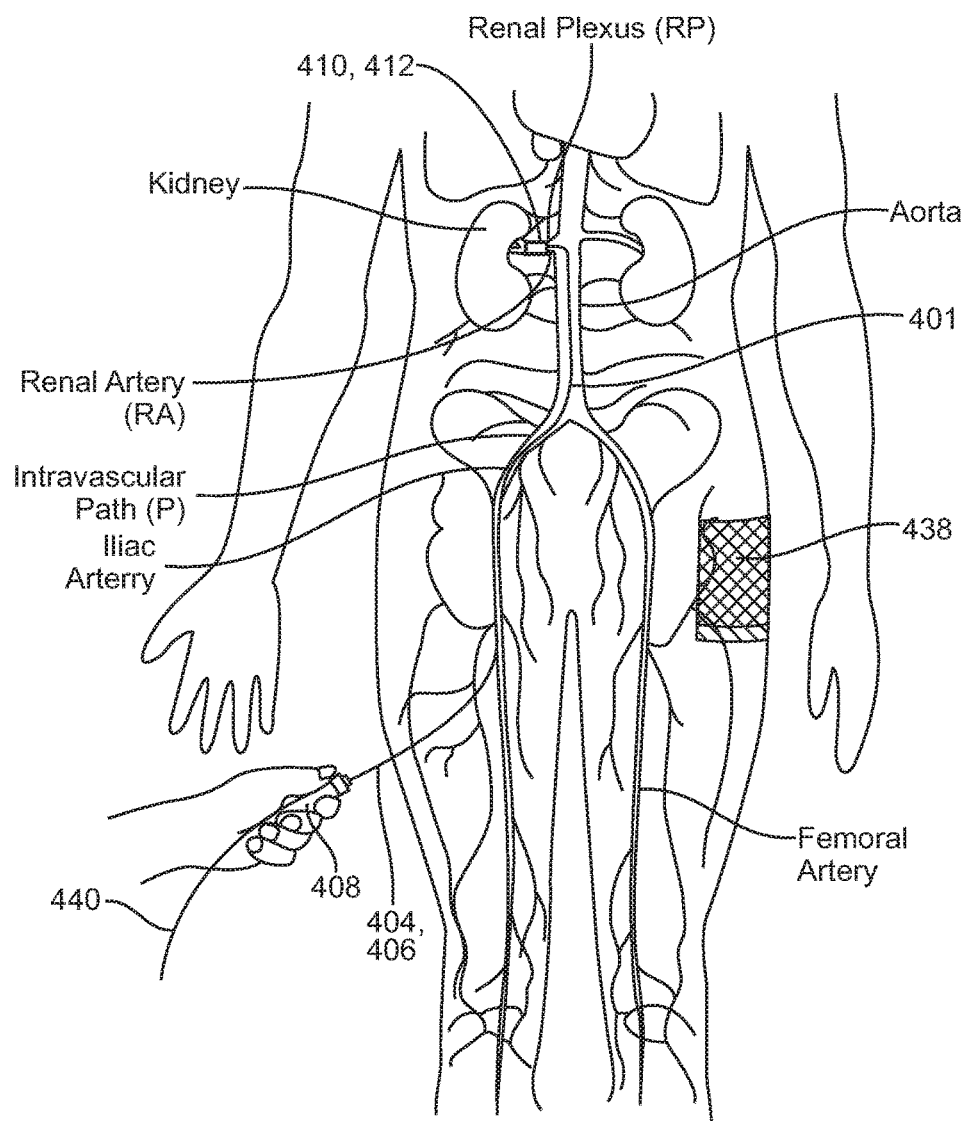
FIG. 5 illustrates modulating renal nerves with a catheter apparatus configured in accordance with an embodiment of the present technology.

FIG. 5 (with additional reference to FIG. 4) illustrates modulating renal nerves with an embodiment of the system 400. The catheter 401 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 406 of the shaft 404 is exposed externally of the patient. By manipulating the proximal portion 406 of the shaft 404 from outside the intravascular path P, the clinician may advance the shaft 404 through the sometimes tortuous intravascular path P and remotely manipulate the distal portion 410 of the shaft 404. In the embodiment illustrated in FIG. 5, the therapeutic assembly 412 is delivered intravascularly to the treatment site using a guide wire 440 in an OTW technique. As noted previously, the distal end of the therapeutic assembly 412 may define a lumen or passageway for receiving the guide wire 440 for delivery of the catheter 401 using either OTW or RX techniques. At the treatment site, the guide wire 401 can be at least partially axially withdrawn or removed, and the therapeutic assembly 412 can transform or otherwise be moved to a deployed arrangement for delivering energy at the treatment site as described above with respect to FIGS. 1A-3. The guide wire 440 may comprise any suitable medical guide wire sized to slideably fit within the lumen. In one particular embodiment, for example, the guide wire 440 may have a diameter of 0.356 mm (0.014 inch). In other embodiments, the therapeutic assembly 412 may be delivered to the treatment site within a guide sheath (not shown) with or without using the guide wire 440. When the therapeutic assembly 412 is at the target site, the guide sheath may be at least partially withdrawn or retracted and the therapeutic assembly 412 can be transformed into the deployed arrangement. In still other embodiments, the shaft 404 may be steerable itself such that the therapeutic assembly 412 may be delivered to the treatment site without the aid of the guide wire 440 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the therapeutic assembly 412. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the catheter 401. Further, in some embodiments, image guidance components (e.g., IVUS, OCT) may be integrated with the catheter 401 and/or run in parallel with the catheter 401 to provide image guidance during positioning of the therapeutic assembly 412. For example, image guidance components (e.g., IVUS or OCT) can be coupled to at least one of the therapeutic assembly 412 to provide three-dimensional images of the vasculature proximate the target site to facilitate positioning or deploying the therapeutic assembly 412 within the target renal blood vessel.

Referring to FIGS. 4 and 5 together, the purposeful application of energy from the energy delivery portions 418 (e.g., the exposed regions of the energy delivering thermocouple wire) may be applied to target tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery portions 418 (FIG. 4) and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

In operation (and with reference to FIGS. 1A-5), after being positioned at a desired location within the renal artery RA of the patient, the therapeutic assembly 412 may be transformed from its delivery state (e.g., delivery state 101 shown in FIG. 1B) to its deployed state (e.g., deployed state 103 shown in FIG. 1C). The transformation may be initiated using an arrangement of device components as described herein with respect to the particular embodiments and their various modes of deployment. In one embodiment, for example, the therapeutic assembly 412 may be deployed by retracting the guide wire 440 until a distal tip of the guide wire 440 is generally aligned with the tip 420 of the catheter 401. In some embodiments, the guide wire 440 may have a varying stiffness or flexibility along its length so as to provide increased flexibility distally. When the varying flexible guide wire 440 is partially retracted as described above, the pre-set spiral shape of the control member 124 (FIG. 1A) provides a shape-recovery force sufficient to overcome the straightening force provided by the distalmost portion of the guide wire 440 such that the therapeutic assembly 412 can deploy into its spiral configuration. Further, because the flexible distal portion of the guide wire 440 remains within the therapeutic assembly 412 in the deployed state 101 (e.g., FIGS. 1B and 2C), the guide wire 440 can impart additional structural integrity to the spiral-shaped portion during treatment. This feature is expected to help mitigate or reduce problems associated with keeping the therapeutic assembly 412 in place during treatment (e.g., help with vasoconstriction).

In another embodiment, the guide wire 440 may have a stiffness profile that permits the distal portion of the guide wire 440 to remain extended from an opening (not shown) in the tip 420 while still permitting the therapeutic assembly 412 to transform to its deployed state (e.g., deployed state 103 shown in FIG. 1C). In still other embodiments, the guide wire 440 may be withdrawn completely from the therapeutic assembly 412 (e.g., a distalmost end portion of the guide wire 440 is proximal of the therapeutic assembly 412) to permit the transformation, while a distalmost portion of the guide wire 440 remains within the shaft 404. In yet another embodiment, the guide wire 440 may be withdrawn completely from the shaft 404. In any of the foregoing examples, the clinician can withdraw the guide wire 440 sufficiently to observe transformation of the therapeutic assembly 412 to the deployed configuration and/or until an X-ray image shows that the distal tip of the guide wire 440 is at a desired location relative to the therapeutic assembly 412 (e.g., generally aligned with the tip 420, completely withdrawn from the therapeutic assembly 412, etc.). In some embodiments, the extent of withdrawal for the guide wire 440 can be based, at least in part, on the clinician's judgment with respect to the selected guide wire and the extent of withdrawal necessary to achieve deployment.

After treatment, the therapeutic assembly 412 may be transformed back to the low-profile delivery configuration by axially advancing the guide wire 440 relative to the therapeutic assembly 412. In one embodiment, for example, the guide wire 440 may be advanced until the distal tip of the guide wire 440 is generally aligned with the tip 420, and the catheter 401 can then be pulled back over the stationary guide wire 440. In other embodiments, however, the distalmost portion of the guide wire 440 may be advanced to a different location relative to the therapeutic assembly 412 to achieve transformation of the therapeutic assembly 412 back to a low-profile arrangement.

Neuromodulation

Neuromodulation is the partial or complete incapacitation or other effective disruption of nerves innervating, for example, an organ. As an example, renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over-stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves.

Various techniques can be used to partially or completely incapacitate neural pathways, such as those innervating the kidney. The purposeful application of energy (e.g., electrical energy, thermal energy) to tissue by energy delivery element (s) or components such as those described in conjunction with the catheter devices above, can induce one or more desired thermal heating effects on localized regions of the renal artery and adjacent regions of the renal plexus, which lay intimately within or adjacent to the adventitia of the renal artery. The purposeful application of the thermal heating effects can achieve neuromodulation along all or a portion of the renal plexus.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity (RSNA) is expected.

FURTHER EXAMPLES

The following examples are illustrative of several embodiments of the present technology:

1. A method of manufacturing a medical device for neuromodulation (e.g., neuromodulation of renal nerves), the method comprising:
positioning a thermocouple assembly along a distal portion of a catheter, wherein the thermocouple assembly comprises a first wire and a second wire composed of dissimilar metals, and wherein the thermocouple assembly comprises a thermocouple junction at least proximate the distal portion;
wherein the first wire has a plurality of exposed and insulated regions along a portion of the first wire proximate the distal portion, and the second wire of the thermocouple assembly remains insulated; and
wherein the distal portion of the catheter includes an elongated tubular shaft configured to transform between a delivery configuration and a deployed configuration at a target treatment site within a blood vessel of a human patient, and wherein, in the deployed configuration, the exposed regions of the first wire define a plurality of energy delivery portions positioned to deliver electrical energy (e.g., RF energy, pulsed energy) to target tissue adjacent a wall of the blood vessel.

2. The method of example 1 wherein disposing a thermocouple assembly along a distal portion of a catheter comprises helically positioning the thermocouple assembly about the shaft.

3. The method of example 1 or example 2 wherein the shaft comprises a tubular structure having a lumen therethrough and a self-expanding, shape-memory material disposed within the lumen.

4. The method of any one of examples 1-3 wherein the shaft comprises a tubular structure having a lumen therethrough and is composed of a Nitinol multifilar stranded wire.

5. The method of any one of examples 1-4 wherein the method further comprises coating the exposed regions of the first wire with a biocompatible conductive material.

6. The method of any one of examples 1-5 wherein the exposed regions along the first wire of the thermocouple assembly are in electrical communication with each other.

7. The method of any one of examples 1-6, further comprising selectively removing portions of the first wire of the thermocouple assembly to define a plurality of exposed and insulated regions.

8. The method of example 7 wherein selectively removing portions of the first wire of the thermocouple assembly comprises forming four exposed regions along the first wire.

9. The method of any one of examples 1-8 wherein, in the deployed configuration, the shaft carrying the thermocouple assembly comprises a radially expanded, generally spiral shape configured to contact the wall of the blood vessel and to allow blood to flow through the vessel.

10. The method of any one of examples 1-9, further comprising disposing one or more sleeves composed of insulative material about the thermocouple assembly and the shaft.

11. The method of example 10 wherein the sleeves comprise polyethylene terephthalate (PET) heat shrink tubing.

12. The method of any one of examples 1-11 wherein the first wire is composed of copper and the second wire is composed of constantan.

13. The method of any one of examples 1-11 wherein the first wire is composed of silver coated nickel and the second wire is composed of constantan.

14. The method of any one of examples 1-11 wherein the first wire is composed of nickel and the second wire is composed of constantan.

15. The method of any one of examples 1-11 wherein the first wire is composed of silver and the second wire is composed of constantan.

16. A catheter apparatus, comprising:
an elongated tubular shaft in a distal portion of the catheter apparatus, the shaft having a pre-formed spiral shape; and
a therapeutic assembly disposed at the distal portion of the catheter apparatus and adapted to be located at a target location within an artery (e.g., a renal artery) of a human patient, the therapeutic assembly comprising a thermocouple assembly helically wrapped about the shaft, wherein the thermocouple assembly comprises a thermocouple junction at least proximate a distal portion of the shaft, and a first wire and a second wire composed of dissimilar metals, wherein the first wire comprises a plurality of exposed and insulated regions along the shaft, and further wherein the second wire is insulated along the shaft,
wherein the elongated tubular shaft and the therapeutic assembly together define therethrough a guide wire lumen configured to slideably receive a medical guide wire,
wherein axial movement of the guide wire relative to the therapeutic assembly transforms the shaft between (a) a low-profile delivery configuration and (b) a deployed configuration tending to assume the pre-formed spiral shape of the shaft,
wherein, in the deployed configuration, the exposed regions of the first wire define a plurality of energy delivery portions positioned to deliver electrical energy (e.g., RF energy, pulsed energy) to target tissue adjacent a wall of the artery.

17. The catheter apparatus of example 16 wherein, in the deployed configuration, the energy delivery portions of the first wire are spaced apart from each other along a longitudinal axis of the artery and are configured to maintain apposition with a wall of the artery.

18. The catheter apparatus of example 16 or example 17 wherein the shaft comprises a tubular member having a lumen therethrough and is composed of a Nitinol multifilar stranded wire.

19. The catheter apparatus of any one of examples 16-18 wherein the exposed regions along the first wire of the thermocouple assembly do not contact each other in the delivery or deployed configurations.

20. The catheter apparatus of any one of examples 16-19 wherein the individual energy delivery portions are in electrical communication with each other.

21. The catheter apparatus of any one of examples 16-20 wherein the first wire of the thermocouple assembly comprises four energy delivery portions.

22. The catheter apparatus of any one of examples 16-21 wherein the therapeutic assembly does not include any electrodes.

23. The catheter apparatus of any one of examples 16-22 wherein the energy delivery portions are configured to deliver a thermal radiofrequency field to target nerves adjacent the wall of the artery.

24. A catheter system, comprising:
- an electric field generator configured to deliver radiofrequency (RF) energy to target tissue of a human patient;
- a catheter having a distal portion configured for placement within a blood vessel of the patient;
- a treatment assembly at the distal portion of the catheter, wherein the treatment assembly is selectively transformable between a low-profile delivery configuration and a deployed configuration sized to fit within the blood vessel;
- a thermocouple arranged about the distal portion of the catheter and electrically connectable to the electric field generator, wherein the thermocouple comprises—
  - a first conductive wire having a plurality of predefined uninsulated regions at the distal portion of the catheter that define RF energy delivery portions positioned to deliver RF energy to the target tissue when the treatment assembly is in the deployed configuration;
  - a second insulated wire adjacent to the first wire and composed of a different material than the first wire; and
  - a thermocouple junction at least proximate the distal portion of the catheter.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of manufacturing a medical device for neuromodulation, the method comprising:
   - positioning a thermocouple assembly along a distal portion of a catheter, wherein the thermocouple assembly comprises a first wire composed of a first metal and a second wire composed of a second metal, wherein the first metal and second metal are different, and wherein the thermocouple assembly comprises a thermocouple junction at least proximate the distal portion;
   - wherein the first wire has a plurality of exposed and insulated regions along a portion of the first wire proximate the distal portion, and the second wire of the thermocouple assembly remains insulated; and
   - wherein the distal portion of the catheter includes an elongated tubular shaft configured to transform between a delivery configuration and a deployed configuration at a target treatment site within a blood vessel of a human patient, and wherein, the deployed configuration, the exposed regions of the first wire define a plurality of energy delivery portions positioned to deliver energy to target tissue adjacent a wall of the blood vessel.

2. The method of claim 1 wherein positioning the thermocouple assembly along a distal portion of a catheter comprises helically positioning the thermocouple assembly about the shaft.

3. The method of claim 1 wherein the shaft comprises a tubular structure having a lumen therethrough and a self-expanding, shape-memory material disposed within the lumen.

4. The method of claim 1 wherein the shaft comprises a tubular structure having a lumen therethrough and is composed of a Nitinol multifilar stranded wire.

5. The method of claim 1 wherein the method further comprises coating the exposed regions of the first wire with a biocompatible conductive material.

6. The method of claim 1 wherein the exposed regions along the first wire of the thermocouple assembly are in electrical communications with each other.

7. The method of claim 1, further comprising selectively removing portions of the first wire of the thermocouple assembly to define the plurality of exposed and insulated regions.

8. The method of claim 7 wherein selectively removing portions of the first wire of the thermocouple assembly comprises forming four exposed regions along the first wire.

9. The method of claim 1 wherein, in the deployed configuration, the shaft carrying the thermocouple assembly comprises a radially expanded, generally spiral shape configured to contact the wall of the blood vessel and to allow blood to flow through the vessel.

10. The method of claim 1, further comprising disposing one or more sleeves composed of insulative material about the thermocouple assembly and the shaft.

11. The method of claim 10 wherein the one or more sleeves comprise polyethylene terephthalate (PET) heat shrink tubing.

12. The method of claim 1 wherein the first wire is composed of copper and the second wire is composed of constantan.

13. The method of claim 1 wherein the first wire is composed of silver coated nickel and the second wire is composed of constantan.

14. The method of claim 1 wherein the first wire is composed of nickel and the second wire is composed of constantan.

15. The method of claim 1 wherein the first wire is composed of silver and the second wire is composed of constantan.

\* \* \* \* \*